United States Patent [19]

Pang et al.

[11] Patent Number: 5,317,010

[45] Date of Patent: May 31, 1994

[54] PARATHYROID HORMONE ANALOGUES SUBSTITUTED AT AA 25, 26, 27, AND USE IN OSTEOPOROSIS TREATMENT

[75] Inventors: Peter K. T. Pang, University of Alberta, Dept. of Physiology, 7-55 Medical Science Bldg., Edmonton, Canada, T6G 2H7; Jie Shan, Edmonton, Canada

[73] Assignee: Peter K. T. Pang, Edmonton, Canada

[21] Appl. No.: 773,098

[22] Filed: Oct. 10, 1991

[51] Int. Cl.$^5$ .................. A61K 37/36; C07K 7/10
[52] U.S. Cl. .................................. 514/12; 530/324; 530/399; 930/10; 930/DIG. 820; 930/DIG. 821
[58] Field of Search ............... 530/324, 399; 514/12; 930/10, DIG. 820, 821

[56] References Cited

U.S. PATENT DOCUMENTS 4,086,196  4/1978  Tregear ........................ 530/324
4,771,124  9/1988  Rosenblatt .................... 530/324
4,833,125  5/1989  Neer ............................. 514/12

*Primary Examiner*—F. T. Moezie
*Attorney, Agent, or Firm*—Nikaido, Marmelstein, Murray & Oram

[57] ABSTRACT

Analogues of bovine and human parathyroid hormone, wherein twenty-fifth, twenty-six and twenty-seventh positions of the natural hormone, Arg-Lys-Lys- each have been substituted with Ala, Asn, Asp, Cys, Gln, Glu, Gly, His, Ile, Leu, Met, Phe, Pro, Ser, Thr, Trp, Tyr or Val have been found to retain bone cell effect with minimal effects on blood pressure and smooth muscle, including cardiac muscle. It has further been found that this effect can be obtained by using a synthetic PTH containing only the first 34 amino acids of PTH, with substitution at the twenty-fifth, twenty-sixth and twenty-seventh amino acids as described. These analogues of PTH also are effective in the treatment of osteoporosis and other bone diseases.

10 Claims, 19 Drawing Sheets

Fig. 1a

H₂N-<u>Ala</u>-Val-Ser-Glu-Ile-Gln-<u>Phe</u>-Met-His-Asn-Leu-Gly-
Lys-His-Leu-<u>Ser</u>-Ser-Met-Glu-Arg-Val-Glu-<u>Trp</u>-Leu-Arg-
Lys-Lys-Leu-Gln-Asp-Val-His-Asn-Phe-Val-<u>Ala</u>-Leu-Gly-
Ala-Ser-Ile-Ala-Tyr-Arg-Asp-Gly-Ser-Ser-Gln-Arg-Pro-
Arg-Lys-Lys-Glu-Asp-Asn-Val-Leu-Val-Glu-Ser-His-Gln-
Lys-Ser-Leu-Gly-Glu-Ala-Asp-Lys-Ala-Asp-Val-Asp-Val-
Leu-Ile-Lys-Ala-Lys-Pro-Gln-CO₂H

Fig. 1b

H₂N-<u>Ser</u>-Val-Ser-Glu-Ile-Gln-<u>Leu</u>-Met-His-Asn-Leu-Gly-
Lys-His-Leu-<u>Asn</u>-Ser-Met-Glu-Arg-Val-Glu-<u>Trp</u>-Leu-Arg-
Lys-Lys-Leu-Gln-Asp-Val-His-Asn-Phe-Val-<u>Ala</u>-Leu-Gly-
Ala-Ser-Ile-Ala-Tyr-Arg-Asp-Gly-Ser-Ser-Gln-Arg-Pro-
Arg-Lys-Lys-Glu-Asp-Asn-Val-Leu-Val-Glu-Ser-His-Gln-
Lys-Ser-Leu-Gly-Glu-Ala-Asp-Lys-Ala-Asp-Val-Asp-Val-
Leu-Ile-Lys-Ala-Lys-Pro-Gln-CO₂H

Fig. 2

H₂N-<u>Ala</u>-Val-Ser-Glu-Ile-Gln-<u>Phe</u>-Met-His-Asn-Leu-Gly-
Lys-His-Leu-<u>Ser</u>-Ser-Met-Glu-Arg-Val-Glu-Trp-Leu-<u>Xaa</u>-
<u>Xaa</u>-<u>Xaa</u>-Leu-Gln-Asp-Val-His-Asn-Phe-CO₂H

Fig. 3

H₂N-<u>Ala</u>-Val-Ser-Glu-Ile-Gln-<u>Phe</u>-Met-His-Asn-Leu-Gly-
Lys-His-Leu-<u>Ser</u>-Ser-Met-Glu-Arg-Val-Glu-Trp-Leu-<u>Ala</u>-
<u>Ala</u>-<u>Ala</u>-Leu-Gln-Asp-Val-His-Asn-Phe-CO₂H

Fig. 4

H₂N-<u>Ser</u>-Val-Ser-Glu-Ile-Gln-<u>Leu</u>-Met-His-Asn-Leu-Gly-
Lys-His-Leu-<u>Asn</u>-Ser-Met-Glu-Arg-Val-Glu-Trp-Leu-<u>Xaa</u>-
<u>Xaa</u>-<u>Xaa</u>-Leu-Gln-Asp-Val-His-Asn-Phe-CO₂H

Fig. 5

H₂N-<u>Ser</u>-Val-Ser-Glu-Ile-Gln-<u>Leu</u>-Met-His-Asn-Leu-Gly-
Lys-His-Leu-<u>Asn</u>-Ser-Met-Glu-Arg-Val-Glu-Trp-Leu-<u>Ala</u>-
<u>Ala</u>-<u>Ala</u>-Leu-Gln-Asp-Val-His-Asn-Phe-CO₂H

Fig. 6

H$_2$N-<u>Ala</u>-Val-Ser-Glu-Ile-Gln-<u>Phe</u>-Met-His-Asn-Leu-Gly-
Lys-His-Leu-<u>Ser</u>-Ser-Met-Glu-Arg-Val-Glu-Trp-Leu-<u>Xaa</u>-
<u>Xaa</u>-<u>Xaa</u>-Leu-Gln-Asp-Val-His-Asn-Phe-Val-Ala-Leu-Gly-
Ala-Ser-Ile-Ala-Tyr-Arg-Asp-Gly-Ser-Ser-Gln-Arg-Pro-
Arg-Lys-Lys-Glu-Asp-Asn-Val-Leu-Val-Glu-Ser-His-Gln-
Lys-Ser-Leu-Gly-Glu-Ala-Asp-Lys-Ala-Asp-Val-Asp-Val-
Leu-Ile-Lys-Ala-Lys-Pro-Gln-CO$_2$H

Fig. 7

H$_2$N-<u>Ala</u>-Val-Ser-Glu-Ile-Gln-<u>Phe</u>-Met-His-Asn-Leu-Gly-
Lys-His-Leu-<u>Ser</u>-Ser-Met-Glu-Arg-Val-Glu-Trp-Leu-<u>Ala</u>-
<u>Ala</u>-<u>Ala</u>-Leu-Gln-Asp-Val-His-Asn-Phe-Val-Ala-Leu-Gly-
Ala-Ser-Ile-Ala-Tyr-Arg-Asp-Gly-Ser-Ser-Gln-Arg-Pro-
Arg-Lys-Lys-Glu-Asp-Asn-Val-Leu-Val-Glu-Ser-His-Gln-
Lys-Ser-Leu-Gly-Glu-Ala-Asp-Lys-Ala-Asp-Val-Asp-Val-
Leu-Ile-Lys-Ala-Lys-Pro-Gln-CO$_2$H

Fig. 8

H$_2$N-<u>Ser</u>-Val-Ser-Glu-Ile-Gln-<u>Leu</u>-Met-His-Asn-Leu-Gly-
Lys-His-Leu-<u>Asn</u>-Ser-Met-Glu-Arg-Val-Glu-Trp-Leu-<u>Xaa</u>-
<u>Xaa</u>-<u>Xaa</u>-Leu-Gln-Asp-Val-His-Asn-Phe-Val-Ala-Leu-Gly-
Ala-Ser-Ile-Ala-Tyr-Arg-Asp-Gly-Ser-Ser-Gln-Arg-Pro-
Arg-Lys-Lys-Glu-Asp-Asn-Val-Leu-Val-Glu-Ser-His-Gln-
Lys-Ser-Leu-Gly-Glu-Ala-Asp-Lys-Ala-Asp-Val-Asp-Val-
Leu-Ile-Lys-Ala-Lys-Pro-Gln-CO$_2$H

Fig. 9

H$_2$N-<u>Ser</u>-Val-Ser-Glu-Ile-Gln-<u>Leu</u>-Met-His-Asn-Leu-Gly-
Lys-His-Leu-<u>Asn</u>-Ser-Met-Glu-Arg-Val-Glu-Trp-Leu-<u>Ala</u>-
<u>Ala</u>-<u>Ala</u>-Leu-Gln-Asp-Val-His-Asn-Phe-Val-Ala-Leu-Gly-
Ala-Ser-Ile-Ala-Tyr-Arg-Asp-Gly-Ser-Ser-Gln-Arg-Pro-
Arg-Lys-Lys-Glu-Asp-Asn-Val-Leu-Val-Glu-Ser-His-Gln-
Lys-Ser-Leu-Gly-Glu-Ala-Asp-Lys-Ala-Asp-Val-Asp-Val-
Leu-Ile-Lys-Ala-Lys-Pro-Gln-CO$_2$H

1

PARATHYROID HORMONE ANALOGUES SUBSTITUTED AT AA 25, 26, 27, AND USE IN OSTEOPOROSIS TREATMENT

FIELD OF THE INVENTION

This invention relates to analogues of parathyroid hormone which, by substitution at the twenty-fifth, twenty-six and twenty-seventh positions of natural parathyroid hormone, have been found to affect calcium change in bone cells without producing the typical effects of parathyroid hormone on systolic and diastolic blood pressure, the effects on smooth muscle relaxation, vascular smooth muscle calcium change as well as positive chronotropic and inotropic effects on the heart.

BACKGROUND OF THE INVENTION

Parathyroid hormone (hereinafter, PTH) is produced by the parathyroid gland and is involved in the control of calcium levels in blood. It is a hypercalcemic hormone, elevating blood calcium levels. PTH is a polypeptide and the amino acid sequences of bovine and human PTH are closely related. Only the residues at locations one, seven and sixteen differ between the two. Synthetic polypeptides containing the first thirty-four residues of PTH may be prepared using the method disclosed by Erickson and Merrifield, *The Proteins*, Neurath et al., Eds., Academic Press, New York, 1976, page 257, preferably as modified by the method of Hodges et al., *Peptide Research*, 1, 19 (1988).

When serum calcium is reduced to below a "normal" level, the parathyroid gland releases PTH and resorption of bone calcium and increased absorption of calcium from the intestine, as well as renal reabsorption of calcium, occur.

The antagonist of PTH is calcitonin, which acts to reduce the level of circulating calcium. PTH is known to stimulate osteoclasts and its activity requires the presence of derivatives of vitamin $D_3$, especially 1,25-dihydroxycholecalciferol.

Intracellular calcium, particularly in the cells of the vascular system, has been shown to affect changes in vascular tension, as can be measured by changes in blood pressure. U.S. patent application Ser. No. 603,745 describes one method which has been discovered to regulate calcium uptake in vascular cells.

Osteoporosis is a progressive disease which is particularly characteristic of postmenopausal women, and results in the reduction of total bone mass. The sequelae frequently involve fractures of load-bearing bones and the physical degenerations characteristic of immobilizing injuries. osteoporosis is associated with hyperthyroidism, hyperparathyroidism, Cushings syndrome and the use of certain steroidal drugs. Remedies historically have involved increase in dietary calcium, estrogen therapy and increased doses of vitamin D.

PTH has been used to treat osteoporosis. However, while the use of PTH is effective in the treatment of osteoporosis by diminishing the loss of bone mass, PTH may exhibit other undesired pharmalogical effects, such as hypotension and smooth muscle relaxation (e.g. relaxation of gastrointestinal organs, uterus, tracheal and vas deferens) as well as positive chronotropic and inotropic effects on the heart. The relaxation effects of PTH on smooth muscle as well as positive chronotropic and inotropic effects of PTH are described in Pang et al, *Trends in Pharmacological Sciences*, Vol. 7, No. 9, pp. 340–341 (September 1986).

U.S. Pat. No. 4,771,124 discloses the property of bovine and human PTH analogues wherein $Trp^{23}$ is substituted by amino acids phenylalanine, leucine, norleucine, valine, tyrosine, beta-naphtylalanine and alpha-naphtylalanine as a PTH antagonist. While it was suggested that these analogues might be useful in the treatment of osteoporosis, it was based on the analogues antagonistic action to PTH. Furthermore, there was no data to indicate the effectiveness these analogues on bone or other tissue. In addition, analogues with substituted at $Trp^{23}$ with leucine, phenylalanine or tyrosine would produce undesired secondary effects of smooth muscle relaxation, vascular smooth muscle calcium change as well as positive chronotropic and inotropic effects on the heart.

Because PTH is a peptide, topical administration would be the preferred method of administration. However, topical application of PTH or the aforementioned analogues which exhibit vasoactivity would likely produce an undesired local vascular reaction. This reaction could be potentially detrimental if, for example, nasal administration is employed.

It is one object of this invention to ameliorate bone loss while preventing smooth muscle relaxation as well as positive chronotropic and inotropic effects on the heart and without significantly changing blood pressure. It is another object of this invention to identify that portion of PTH which is responsible for calcium regulation and that portion which appears to be primarily related to control of blood pressure and smooth muscle action.

BRIEF SUMMARY OF THE INVENTION

Modification of either bovine or human PTH at each of the twenty-fifth, twenty-sixth and twenty-seventh amino acid positions to substitute for -arginine-lysine-lysine- either alanine, asparagine, aspartic acid, cysteine, glutamine, glutamic acid, glycine, histidine, isoleucine, leucine, methionine, phenylalanine, proline, serine, threonine, tryptophan, tyrosine or valine produces substantially no change in systolic and diastolic blood pressure, substantially no change in muscle tension and substantially no change in the rate of contraction and the force of contraction of the heart as compared to native PTH. It also has been observed that the PTH analogue containing only the first thirty-four amino acids, with substitution at the twenty-fifth, twenty-sixth and twenty-seventh positions, is equally effective in the "osteo effect" without changing blood pressure or causing muscle relaxation or positive chronotropic and inotropic effects on the heart.

The analogues of the present invention should be effective in ameliorating bone loss while preventing smooth muscle relaxation as well as positive chronotropic and inotropic effects on the heart and without significantly changing blood pressure.

BRIEF DESCRIPTION OF THE DRAWINGS

FIG. 1a shows the structure of natural bovine PTH (SEQ ID (NO:1).

FIG. 1b shows the structure of natural human PTH (SEQ ID (NO:2).

FIG. 2 shows the structure of BPTH (1–34) with each of positions 25, 26 and 27 substituted with Xaa (SEQ ID NO:3).

FIG. 3 shows the structure of BPTH (1-34) with each of positions 25, 26 and 27 substituted with Ala (SEQ ID NO:4).

FIG. 4 shows the structure of HPTH (1-34) with each of positions 25, 26 and 27 substituted Xaa (SEQ ID NO:5).

FIG. 5 shows the structure of HPTH (1-34) with each of positions 25, 26 and 27 substituted Ala (SEQ ID NO:6).

FIG. 6 shows the structure of BPTH with each of positions 25, 26 and 27 substituted with Xaa (SEQ ID NO:7).

FIG. 7 shows the structure of BPTH with each of positions 25, 26 and 27 substituted with Ala (SEQ ID NO:8).

FIG. 8 shows the structure of HPTH with each of positions 25, 26 and 27 substituted with Xaa (SEQ ID NO:9).

FIG. 9 shows the structure of HPTH with each of positions 25, 26 and 27 substituted with Ala (SEQ ID NO:10).

DETAILED DESCRIPTION OF THE INVENTION

Figure 10:
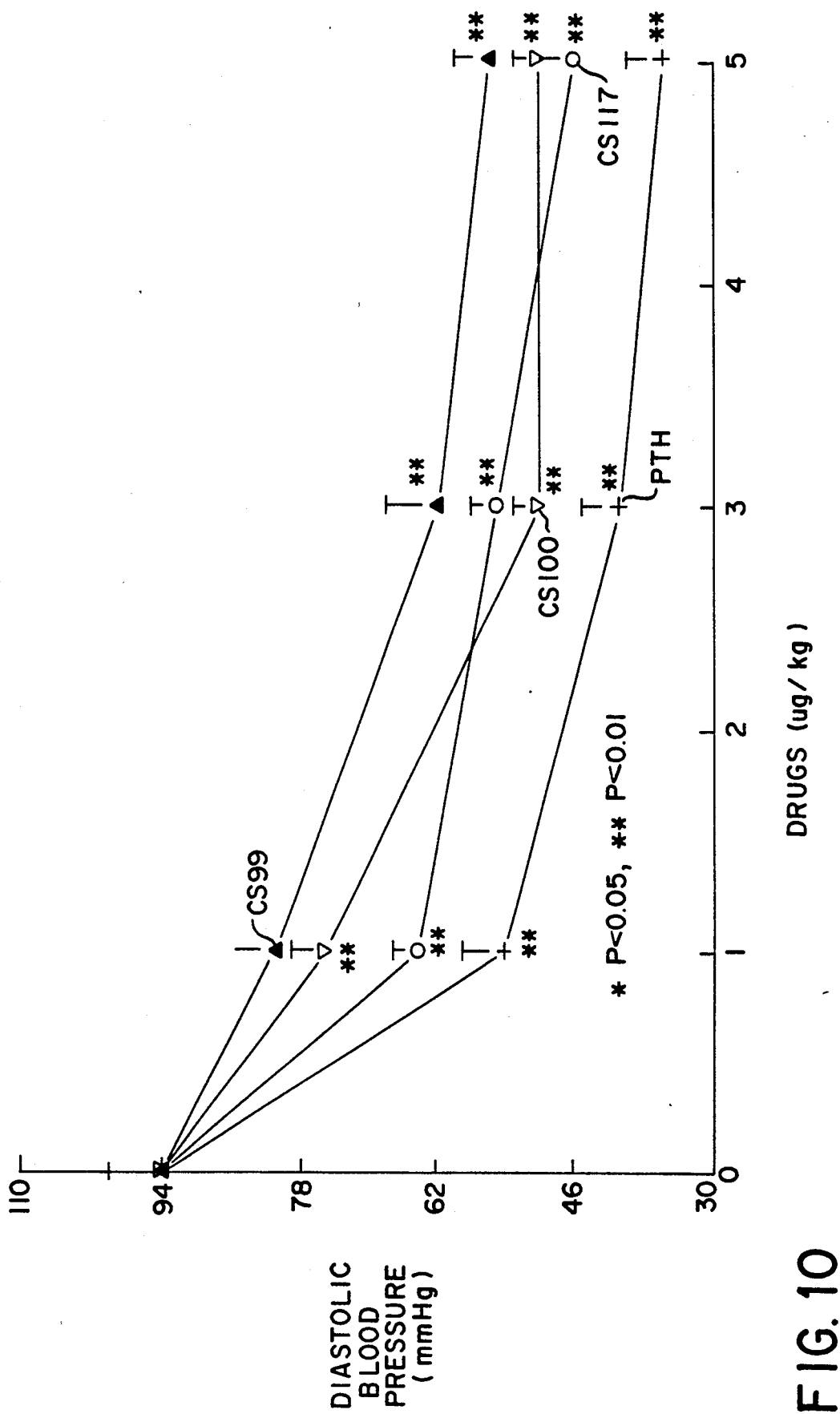
FIG. 10 shows the effect of bPTH-(1-34) and its analogues on diastolic blood pressure of anesthetized Sprague-Dawley rats. The diastolic blood pressure decreases as the dosage of drugs is increased.
Figure 11:
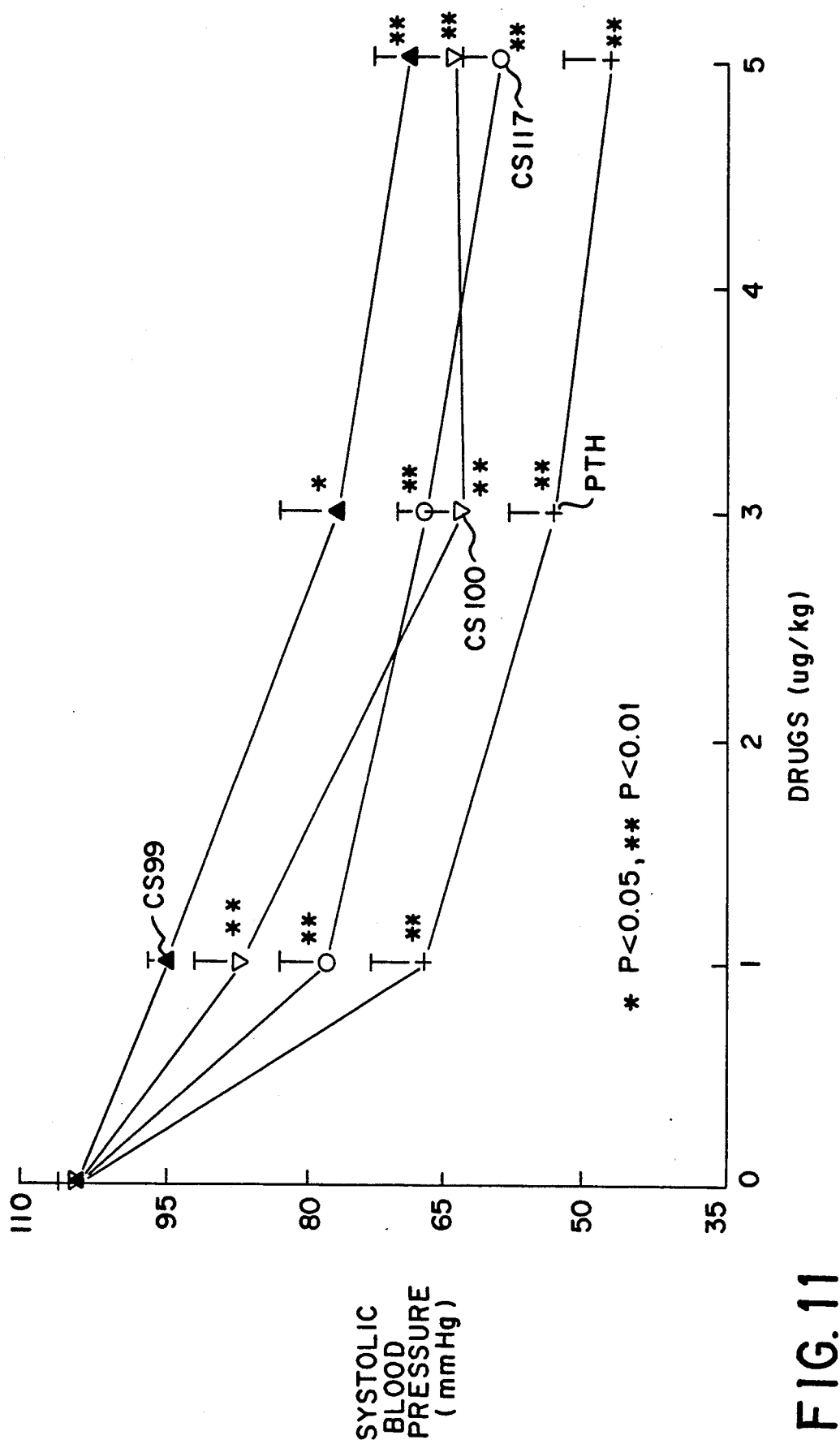
FIG. 11 shows the effect of bPTH-(1-34) and its analogues on systolic blood pressure of anesthetized Sprague-Dawley rats. The systolic blood pressure decreases as the dosage of drugs is increased.

There are at least two known categories of functions for PTH. PTH is involved in calcium balance in the blood stream and controls both the amount of calcium uptake from the gastrointestinal tract and the deposition and removal of calcium from bone. Calcium also has been found to be effective in the maintenance of blood pressure. Cox, *J. Cardiovascular Pharmacology*, Vol. 8 (1986), Supp. 8 S48. Control of calcium in the walls of blood vessels is a useful therapeutic regimen for controlling hypertension and calcium channel blockers, which prevent the introduction of calcium into cell walls, is a conventional therapy for hypertension. Needleman et al. in Goodman and Gilman's *The Pharmacological Basis of Therapeutics*, MacMillan, New York, (1985), page 816 ff.

Administration of therapeutic doses of PTH has been found to be effective for the control of osteoporosis, particularly in individuals who have been subjected to thyroidectomies/parathyroidectomies. Therapeutic dosages of PTH will, in some individuals, result in unacceptable diminution of blood pressure and may result in relaxation of smooth muscles such as gastrointestinal, uterus, tracheal, vas deferens as well as exhibit positive chronotropic and inotropic effects on the heart. To avoid hypotensive effects, smooth muscle relaxation effects and positive chronotropic and inotropic effects on the heart, it was envisaged that the structure of PTH could be modified to decouple the hypotensive, smooth muscle relaxation and positive chronotropic and inotropic function from the bond calcium and bone deposition function. It has now been discovered that a critical site exists at amino acid twenty-five, twenty-six and twenty-seven, which is —Arg—Lys—Lys— in both bovine and human PTH. Substitution at the —Arg—Lys—Lys— site with —Ala—Ala—Ala— diminishes the hypotensive as well as smooth muscle relaxation and positive chronotropic and inotropic effects without denigrating from the osteo effect. These results suggest that substitution at the —Arg—Lys—Lys—site with amino acids other than basic amino acids arginine and lysine would also diminish the hypotensive, smooth muscle relaxation and positive chronotropic and inotropic effects without denigrating from the osteo effect.

The procedure of Erickson and Merrifield, as modified by Hodges et al., as described above, may be used to synthesize synthetic PTH or fragments thereof. The procedure enables substitution for the naturally occurring PTH at substantially every location and it is possible to prepare both bovine and human synthetic PTH at full length or in the sequence of the first thirty-four amino acids, which is more facilely performed. Such substitution can also be accomplished by genetic engineering.

Substitution at position twenty-five, twenty-six and twenty-seven invariably alters the observed hypotensive, smooth muscle relaxation and positive chronotropic and inotropic effects, whether the full length PTH or the 1-34 fragment is administered. Substitution of —Ala—Ala—Ala— for —Arg—Lys—Lys—at position twenty-five, twenty-six and twenty-seven is particularly preferred because the change in blood pressure, smooth muscle relaxation and positive chronotropic and inotropic effects from this substitution are minimal and calcium uptake, as measured in osteoblasts, mimics the results from the administration of native PTH. The 1-34 PTH fragment with —Ala$^{25}$—Ala$^{26}$—Ala$^{27}$— is particularly preferred because the pharmacological properties are those which are desired and the difficulty of synthesis is minimized. Synthesis of the compounds used in the development of this invention was performed at Alberta Peptide Institute (API) and the cooperation of API is gratefully acknowledged.

The structure of bovine parathyroid hormone (BPTH) and human parathyroid hormone (HPTH) are shown in FIGS. 1a (SEQ ID NO:1) and 1b (SEQ ID NO:2). Representative synthetic analogues are described in Table 1 and are further shown in FIGS. 2-9 and SEQ ID NO:3-SEQ ID NO:10. The hypotensive effects of these analogues is shown in FIGS. 10, 11, 15 and 19. All of the analogues produce either no or less diminution of blood pressure than does native PTH. With only one amino acid at either the 25, 26 or 27 position substituted, the analogue shows less effect than native PTH. With all three positions substituted, it provides almost no change. At the level of 5 μg/kg of PTH, the blood pressure in Sprague-Dawley rats is such that they are essentially moribund.

Figure 12:
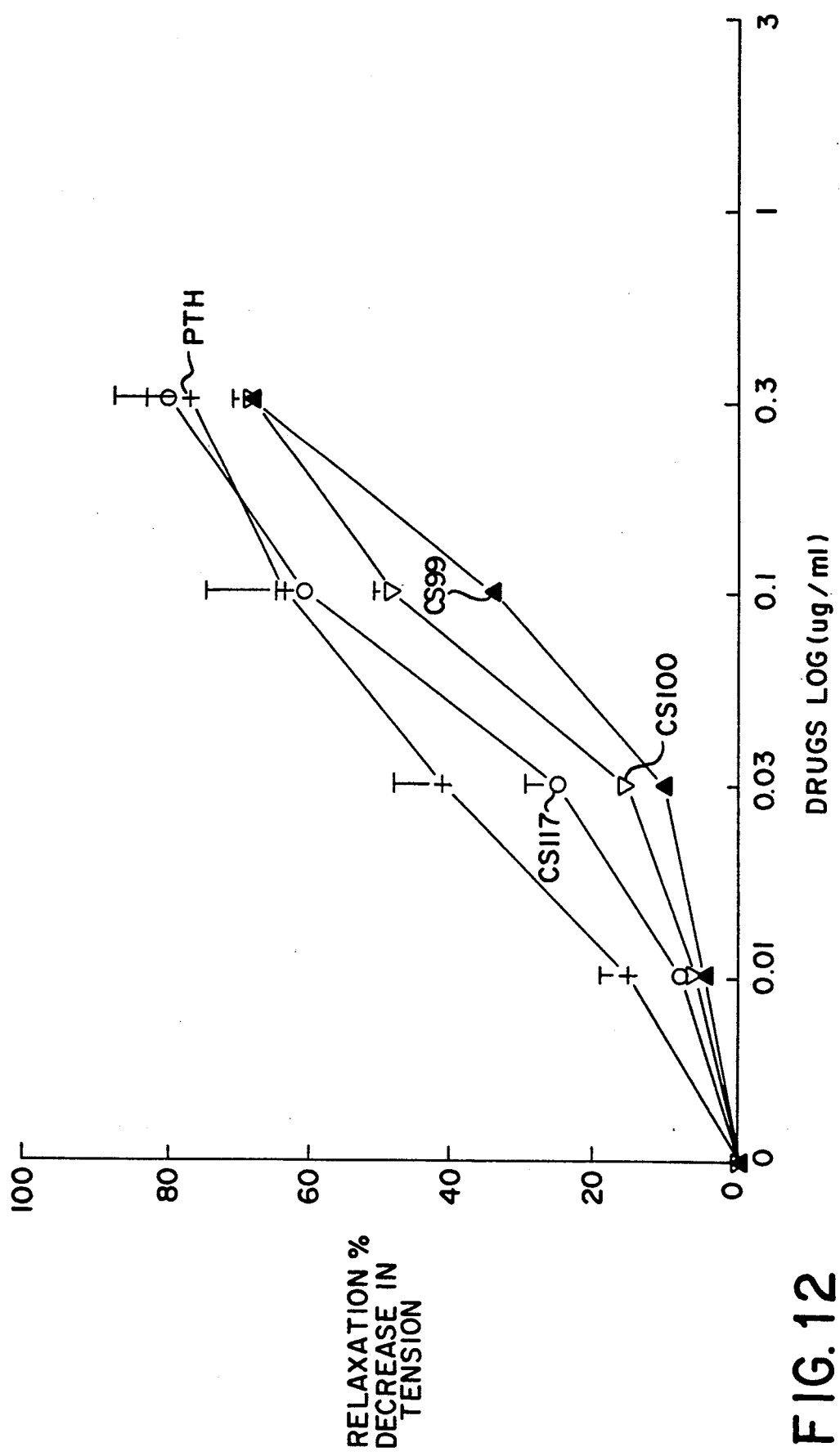
FIG. 12 shows the vasorelaxing effect of bPTH-(1-34) and its analogues on rat tail artery helical strip in vitro. The relaxation of the artery increases as the dosage of drugs is increased.
Figure 16:
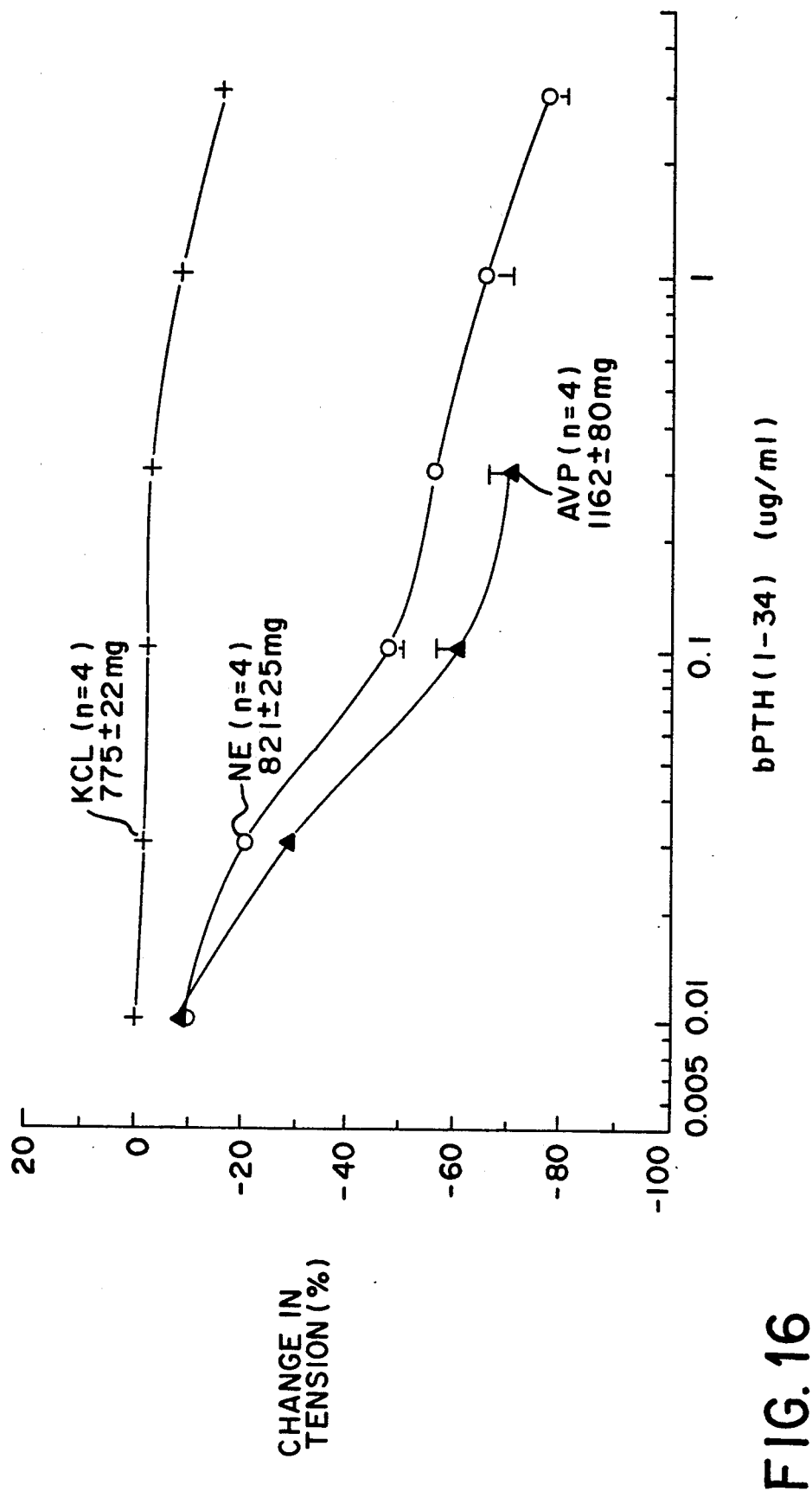
FIG. 16 shows the dose-response relationship between Cs88 [BPTH- (1-34)] and the tension of rat tail artery helical strips precontracted with KCl, norepinephrine and AVP. The tension of the rate tail artery helical strips decreases as the amount of the drug increases.
Figure 17:
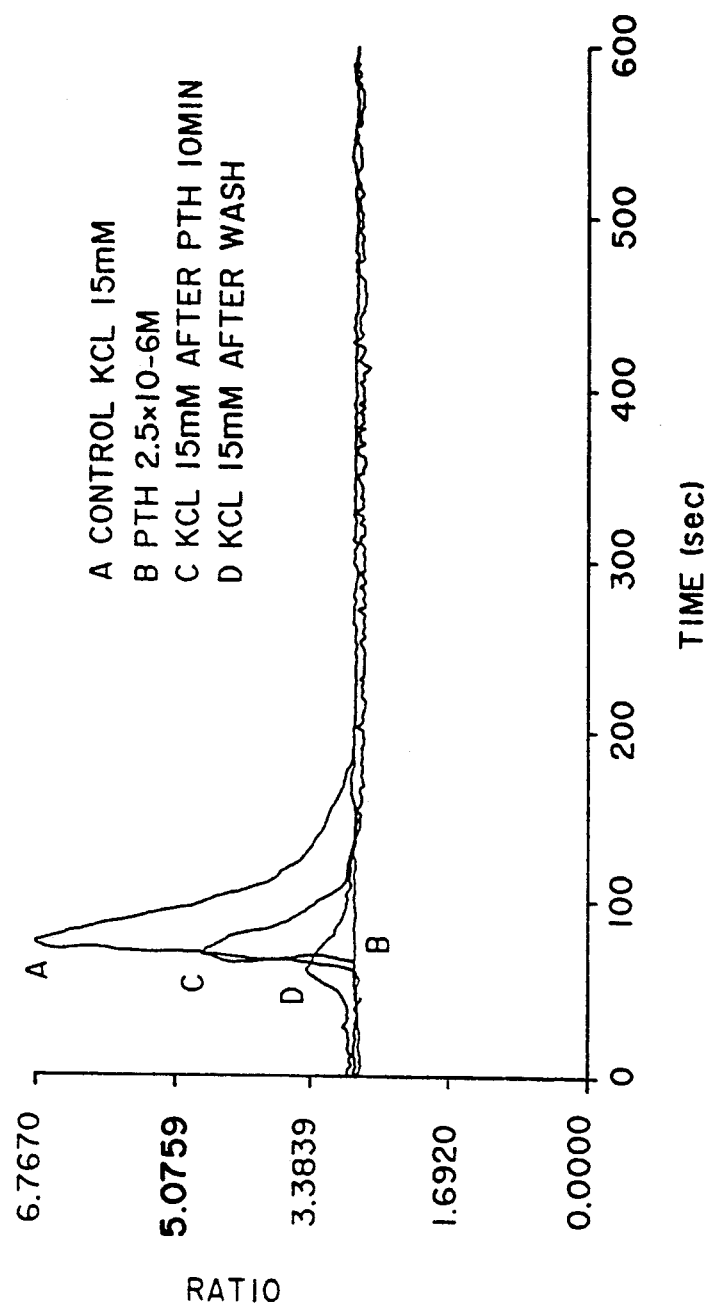
FIG. 17 shows the effect of Cs88 on $[Ca^{2+}]_i$ in cultured UMR osteoblast cells. PTH inhibits intracellular $[Ca^{2+}]_i$ increases as stimulated by KCl.
Figure 18:
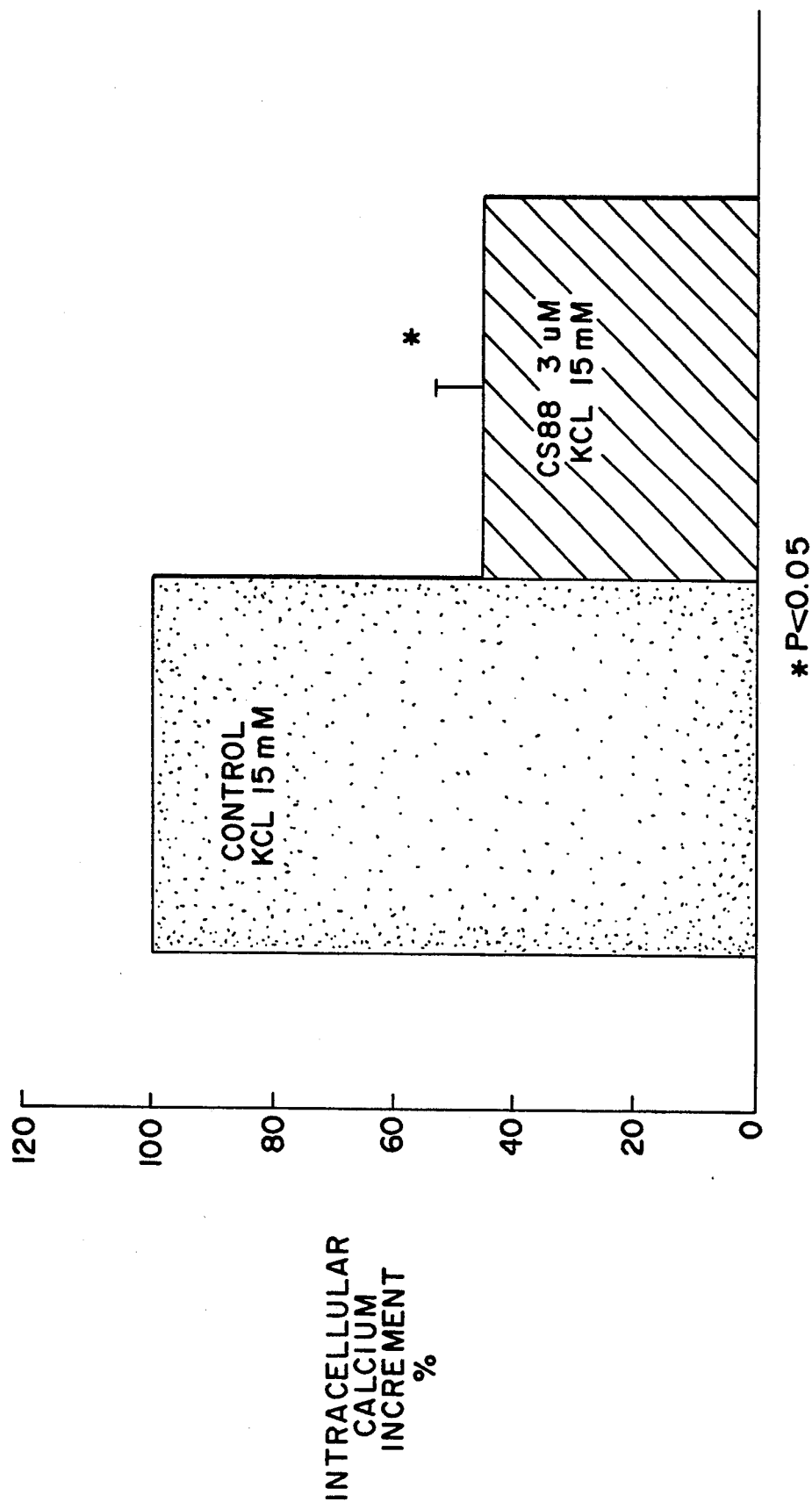
FIG. 18 shows the effect of Cs88 on $(Ca^{2+})_i$ in cultured UMR cells.
Figure 19:
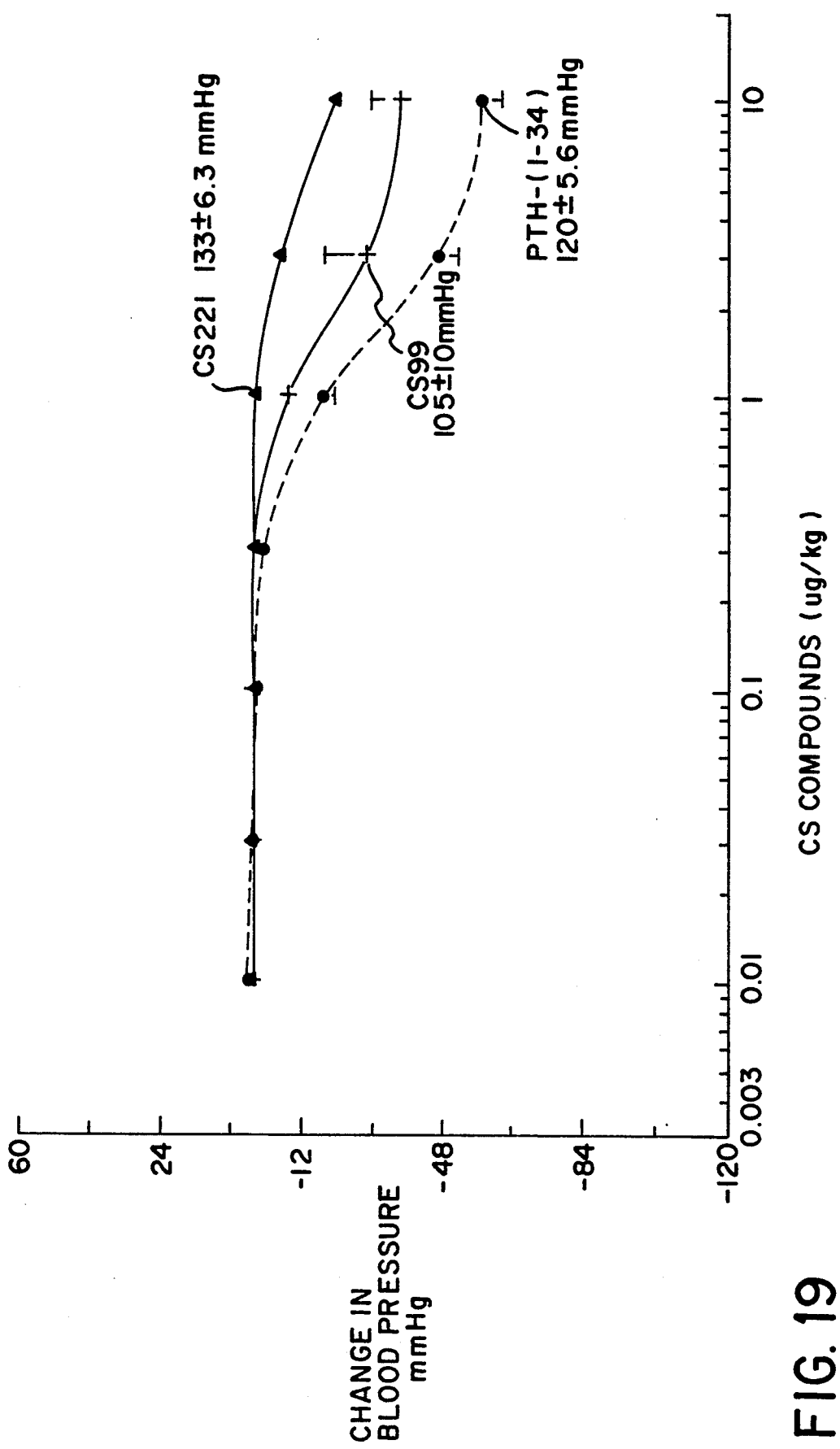
FIG. 19 shows a comparison of the effect of Cs221 and Cs99 and BPTH on the mean arterial blood pressure of anesthetized Sprague-Dawley rats. Cs221 with substitutions at positions 25, 26 and 27 shows the least decrease in blood pressure. Cs99 substituted at position 25, shows more of a decrease in blood pressure but still less than the PTH fragment with no substitutions.
Figure 20:
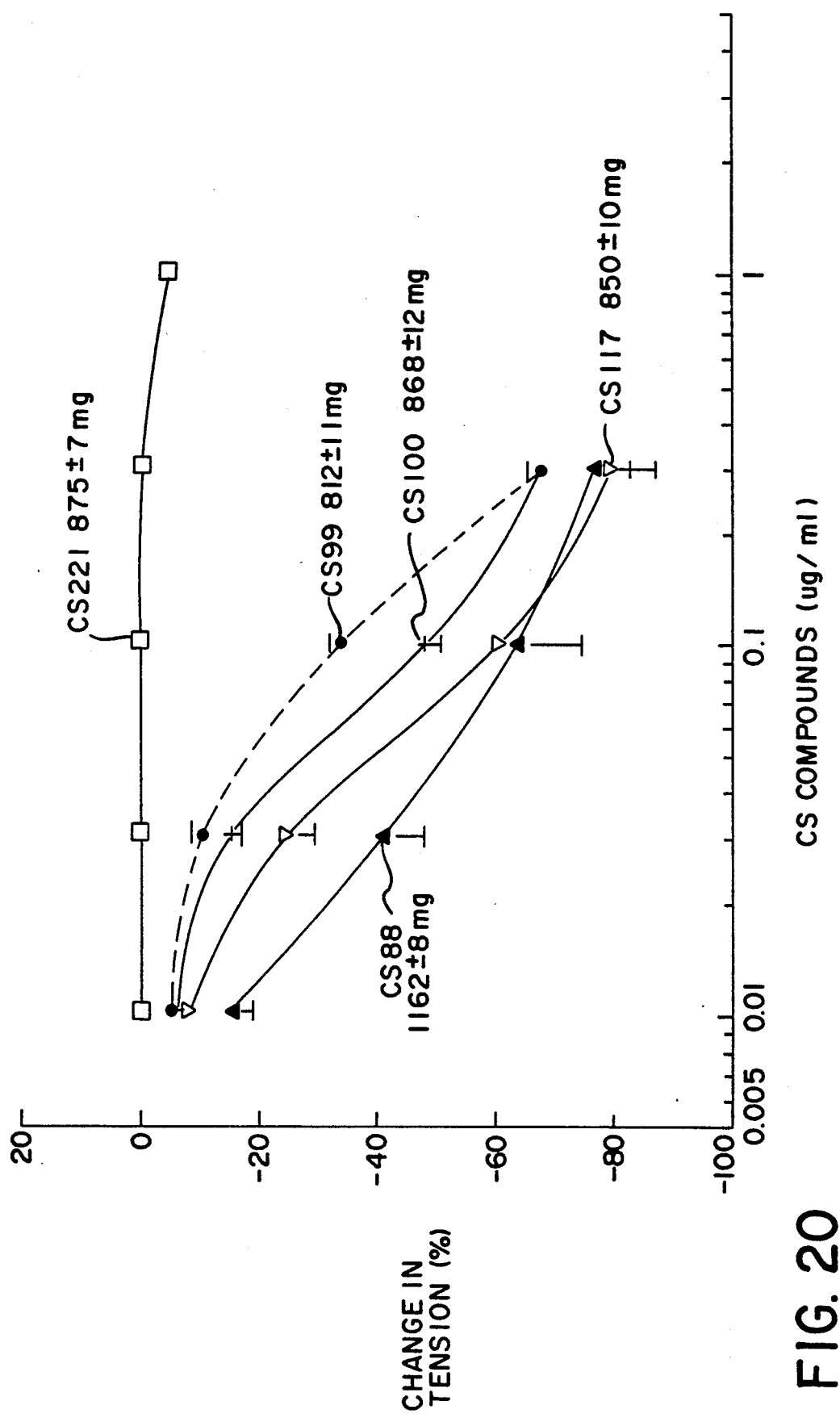
FIG. 20 shows the relation between the relaxation curves of Sprague-Dawley rat tail artery helical strips, precontracted with AVP when treated with Cs100, Cs99, Cs88, Cs117 and Cs221. Cs221 shows the least relaxation of the rat tail artery helical strips as compared with Cs99 (substituted at position 25), Cs100 (substituted at position 26), Cs117 (substituted at position 27) and Cs88 (no substitutions).
Figure 21:
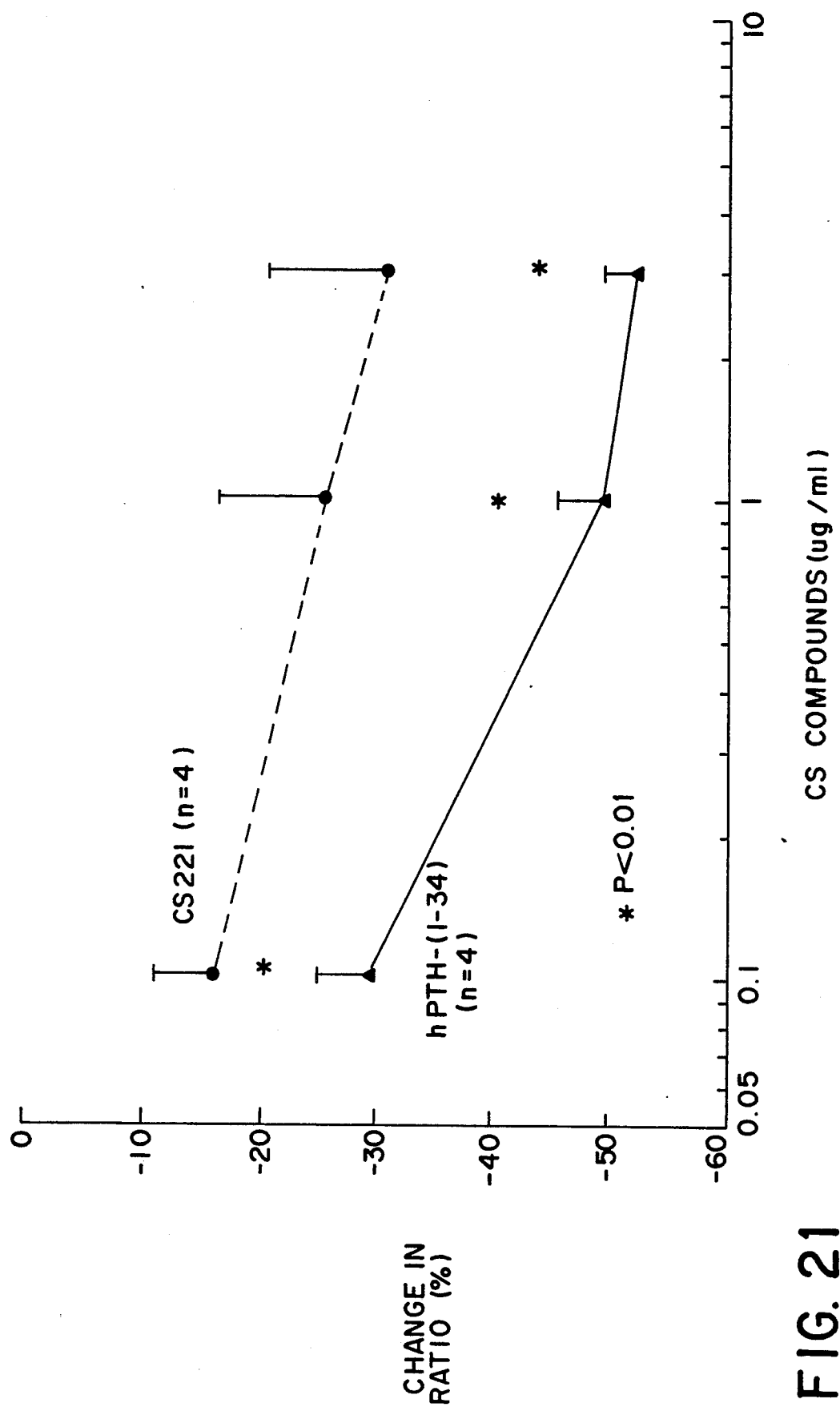
FIG. 21 shows a comparison between the effect of Cs221 and HPTH on the intracellular calcium uptake in the presence of KCl in UMR cells in culture. The inhibition of intracellular $[Ca^{2+}]_i$ increases by Cs221 is comparable to the inhibition of intracellular $[Ca^{2+}]_i$ increases by hPTH.
Figure 22:
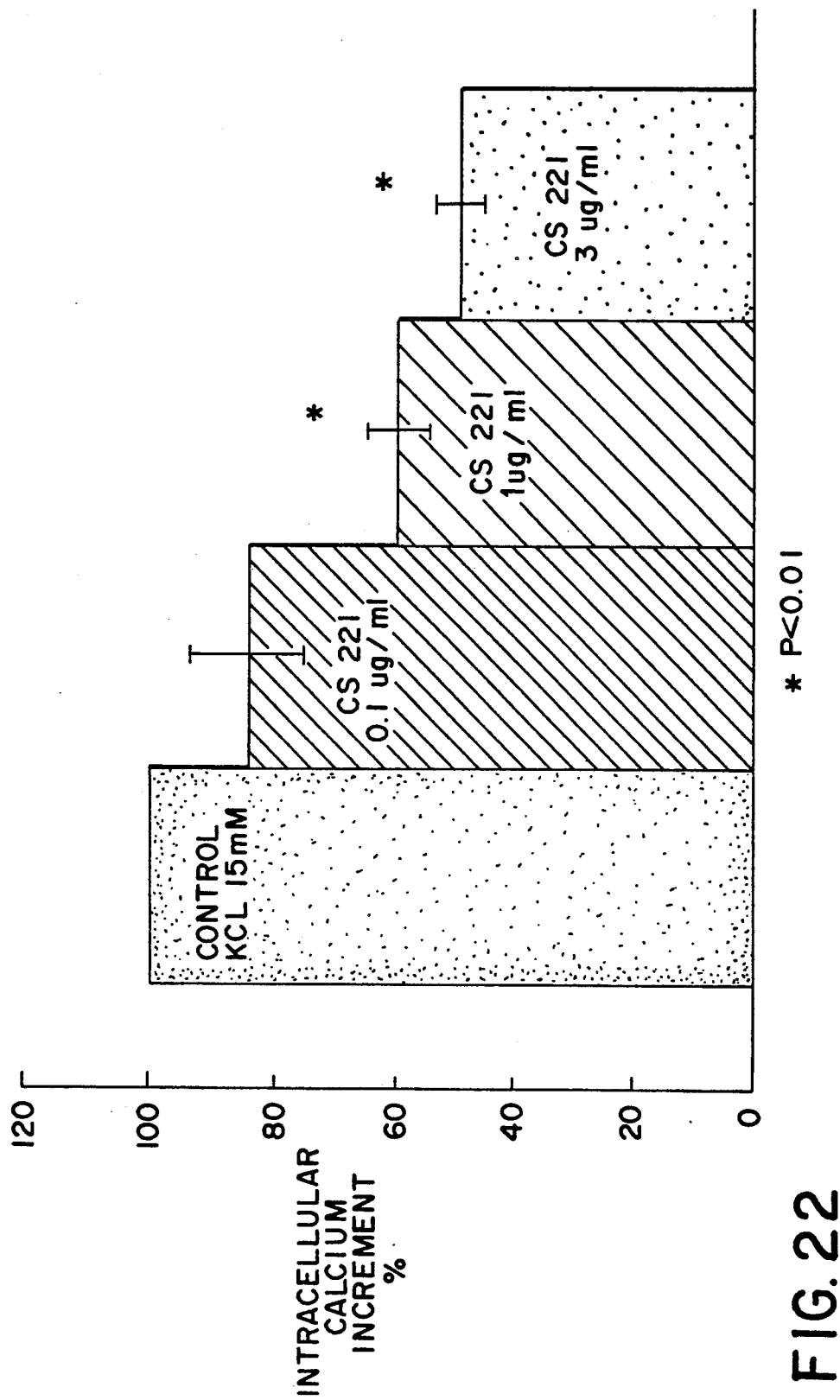
FIG. 22 shows the effect of Cs221 on the intracellular calcium uptake in the presence of KCl in UMR cells in culture. Increasing concentrations of Cs221 produce lower intracellular calcium increments.
Figure 23:
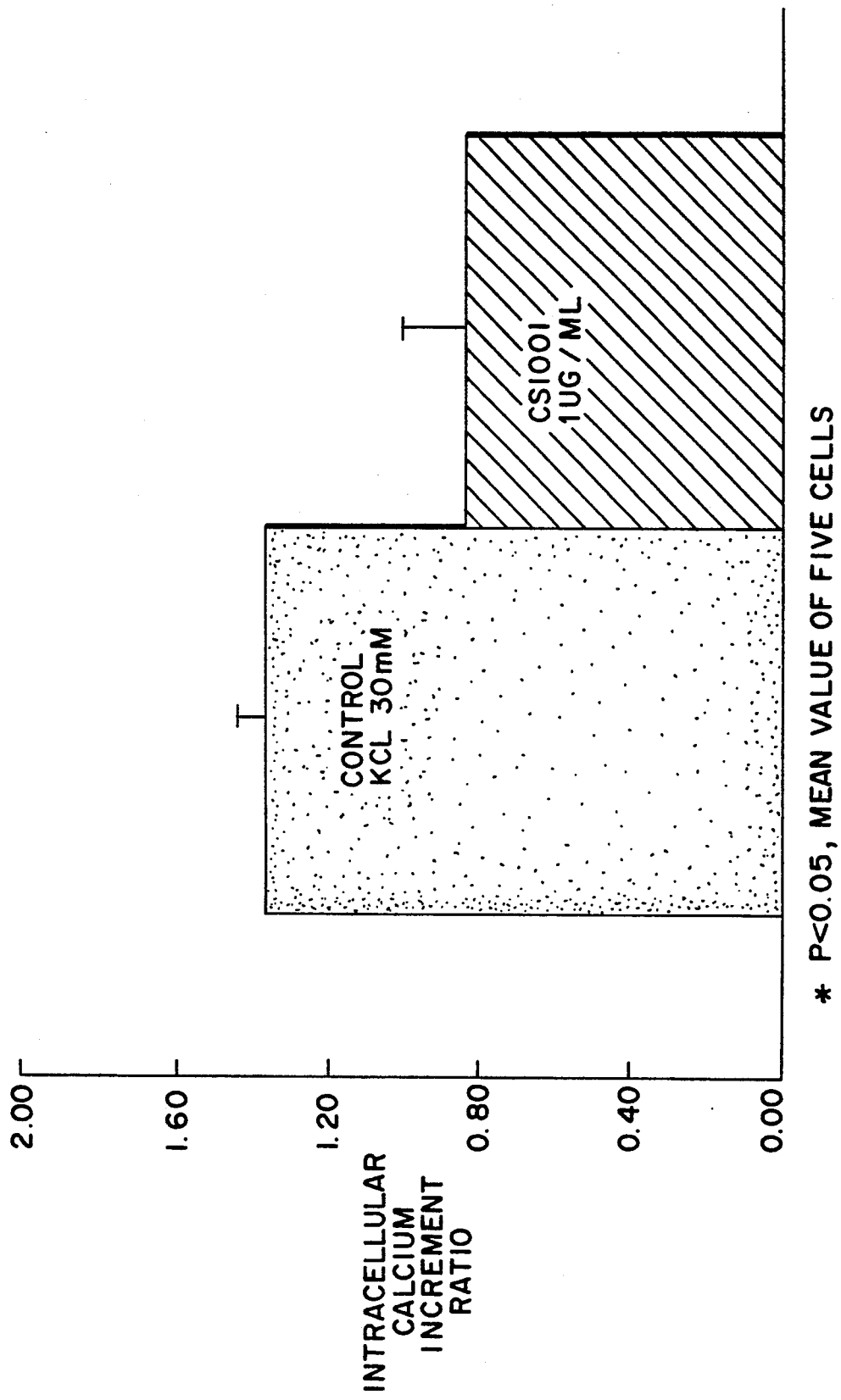
FIG. 23 shows the effect of Cs1001 on the intracellular calcium uptake in the presence of KCl in UMR cells in culture. Increasing concentrations of Cs1001 produce lower intracellular calcium increments.

We have developed a method for modeling the hypotensive effects of natural and synthetic chemical compounds using helically cut tail arteries from Sprague-Dawley rats in a Sawyer-Bartlestone chamber, measuring the change in tension with a force displacement transducer. This method and the effect of bovine PTH-(1-34) in this system is described in Blood Vessels, 22, 57 (1985). It is demonstrated in this paper that bPTH-(1-34) produces dose-dependent relaxation of helical &trips of rat tail artery which have been previously contracted by arginine-vasopressin (AVP). FIGS. 12, 16 and 20 illustrate the effect of the PTH analogues of this invention as measured using this in vitro technique. Alternatively, the strips may be precontracted using other pressor substances such as norepinephrine (NE) or KCl.

Figure 24:
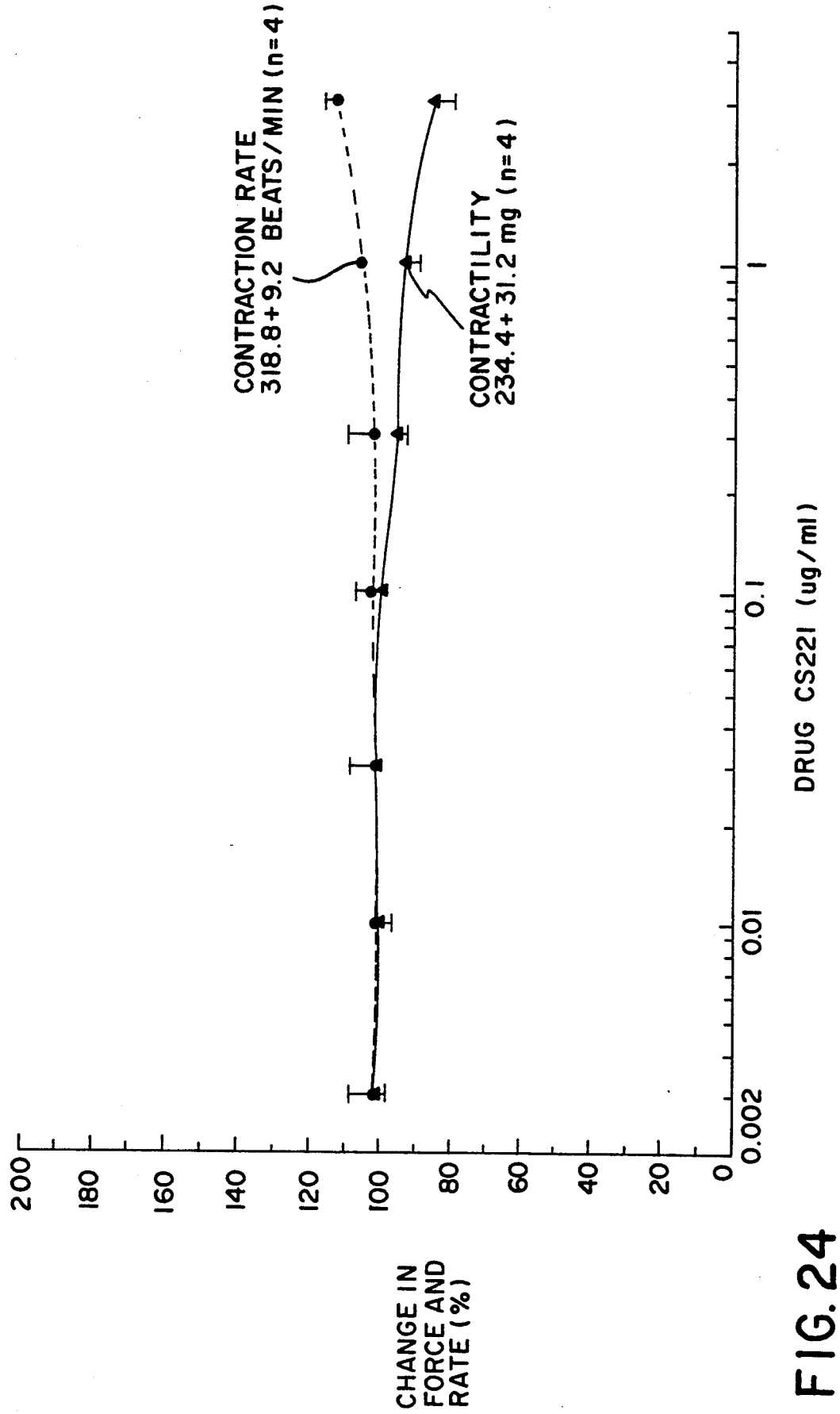
FIG. 24 shows the effect of Cs221 on the contractility and contraction rate of right atrial tissue of Sprague-Dawley rats. Cs221 has minimal effect on the contractility and contraction rate.
Figure 25:
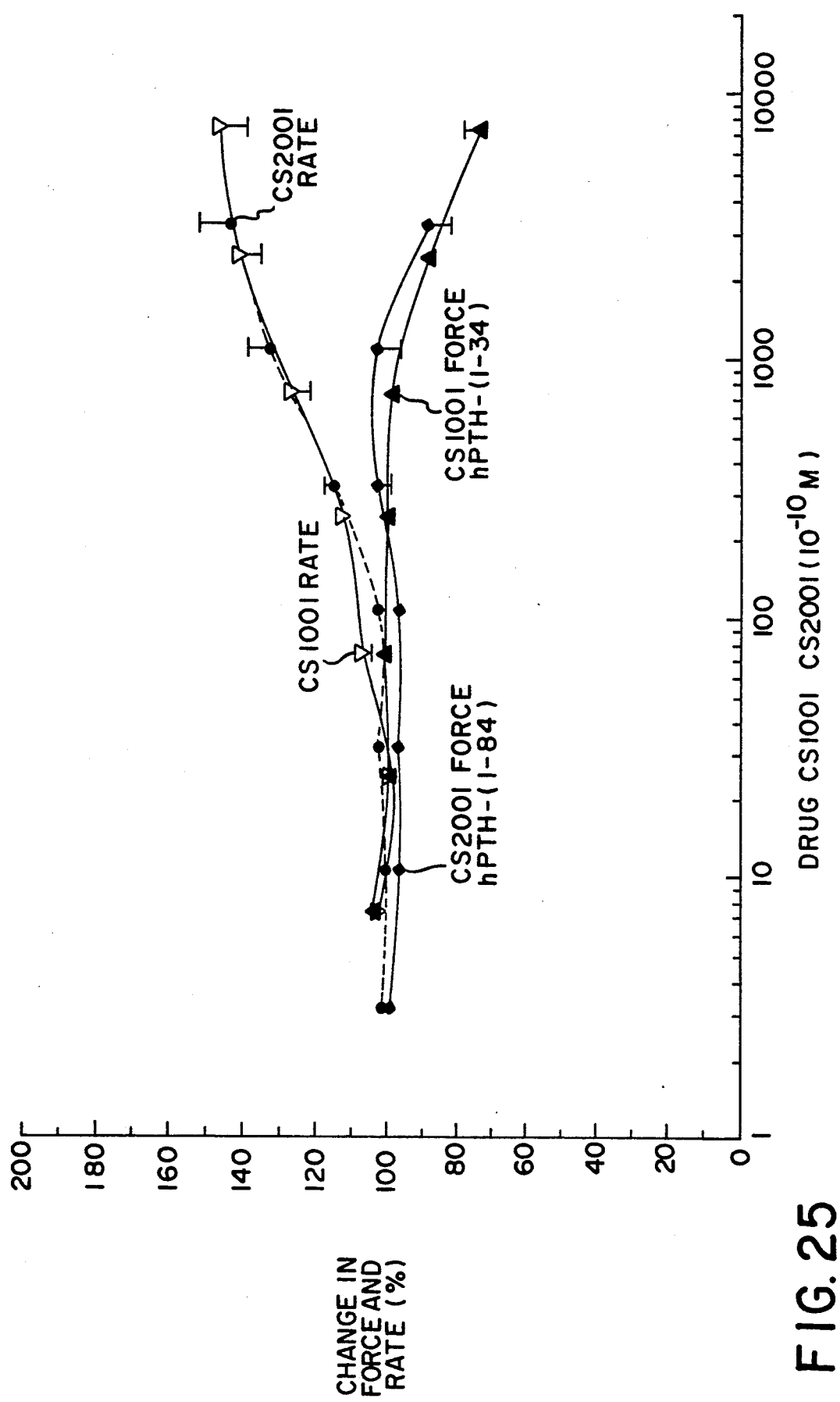
FIG. 25 shows the effect of Cs2001 and Cs1001 on the contractility and contraction rate of right atrial tissue of Sprague-Dawley rats. Both Cs1001 and Cs2001 increase the contraction rate.

We have also developed a method of modeling the chronotropic effects of natural and synthetic chemicals using the right atrium from Sprague-Dawley rats and measuring the change in the force and rate of atrium contraction. This method and the effects of bovine PTH (1-34) in this system are described in Tenner et al, *The Canadian Journal of Physiology and Pharmacology*, Volume 61, No. 10 (1983) pp. 1162-1167. It is demonstrated in this paper that bPTH (1-34) produces significant dose-dependent chronotropic effects on rat cardiac pacemaker tissue. FIGS. 24-25 illustrate the effect of the PTH analogues of this invention as measured using this in vitro technique.

Because osteoporosis is a progressive syndrome, a model is required and the use of cultured osteoblasts of the UMR-106.rat osteosarcoma cells, ATCC CRL 1661 have been used as the model. Uptake of calcium in these cells has been monitored using the FURA-2 method, wherein a fluorescent dye which is specific for calcium is used as a marker for calcium change into the cells. Cells are incubated with 1-10 μM of the acetomethoxy ester of FURA-2 for 30-60 minutes. Upon uptake, the ester is hydrolyzed to release free FURA-2, which selectively binds free $Ca^{2+}$. FURA-2 has a characteristic fluorescence spectrum, which wavelength is shifted when the dye binds to free $Ca^{2+}$. According to the method, $Ca^{2+}$ which is present in the cell can be quantified by exciting the dye at two different wavelengths, 340 and 380 nm. The emission fluorescence is measured at 510 nm. The calcium concentration is proportional to the ratio of the fluorescent emission when excited at 340 nm to the emission at 380 nm. It is conventional to report the concentration of calcium within the cell in terms of the fluorescence ratio, the 340/380 ratio. This technique is described in Grynkiewicz et al., *J. Biol. Chem.*, 260, 3440 (1985) and Pang et al., *P. N. A. S. (USA)*, 87, 623 (1990).

Figure 13:
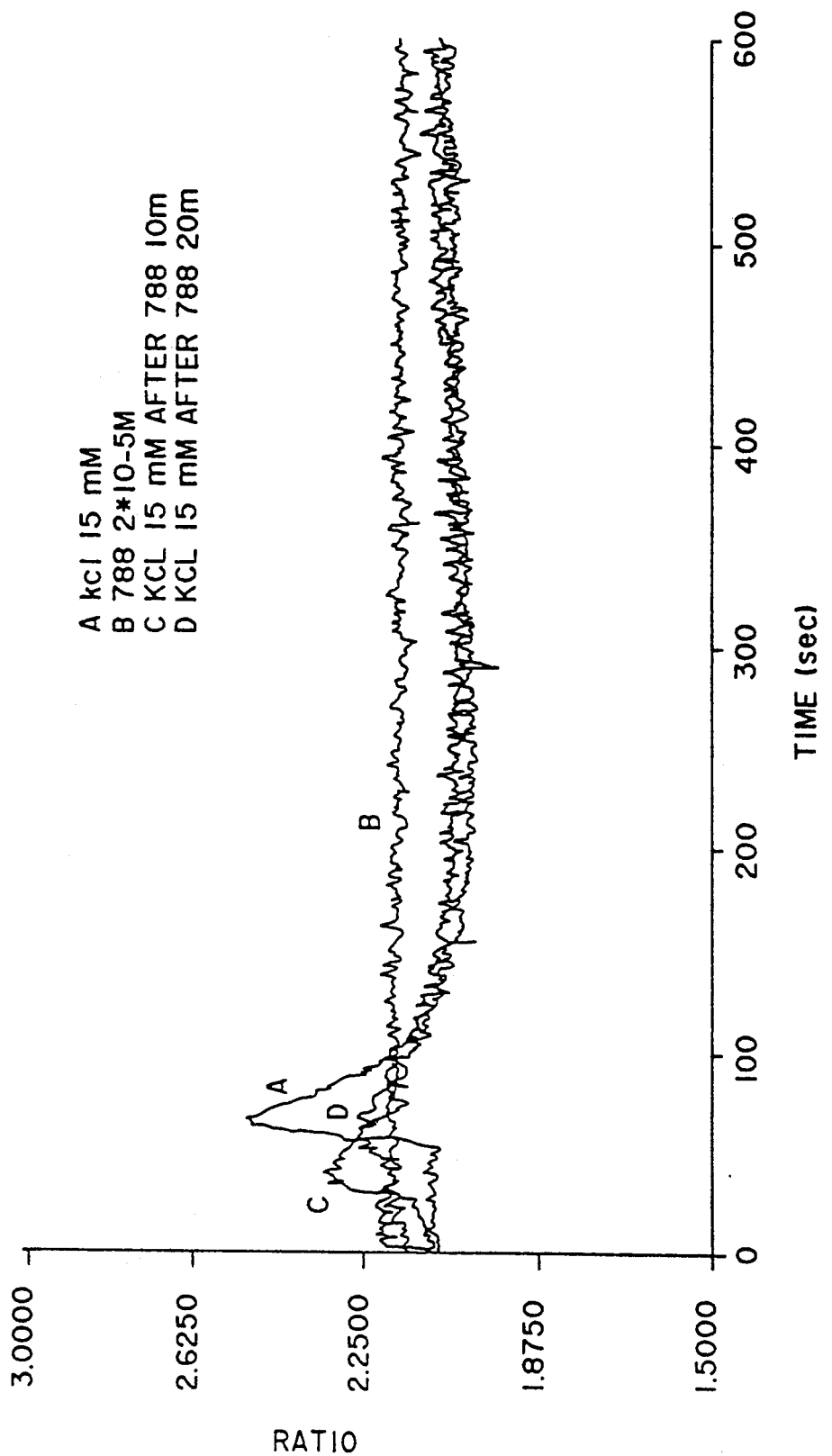
FIG. 13 shows the depolarizing concentrations of KCl which increased calcium ion levels in cultured osteoblasts. Drug 788 is an anti-osteoporotic agent which inhibits the KCl effect.
Figure 14A:
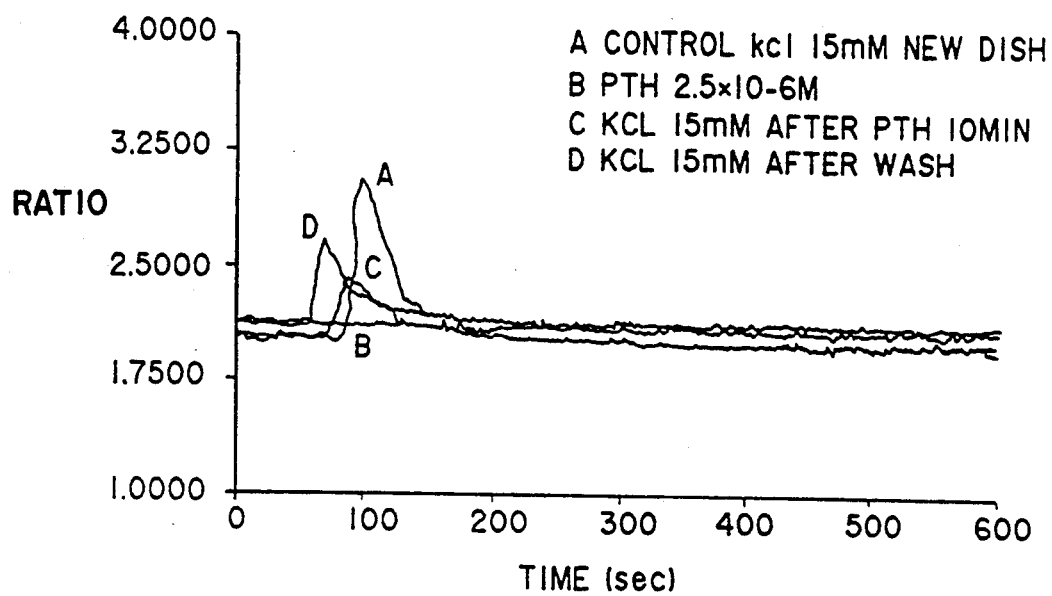
FIGS. 14 a-d show the depolarizing concentrations of KCl which increased calcium levels in cultured osteoblasts. Addition of bPTH-(1-34) inhibits the KCl effect.
Figure 14C:
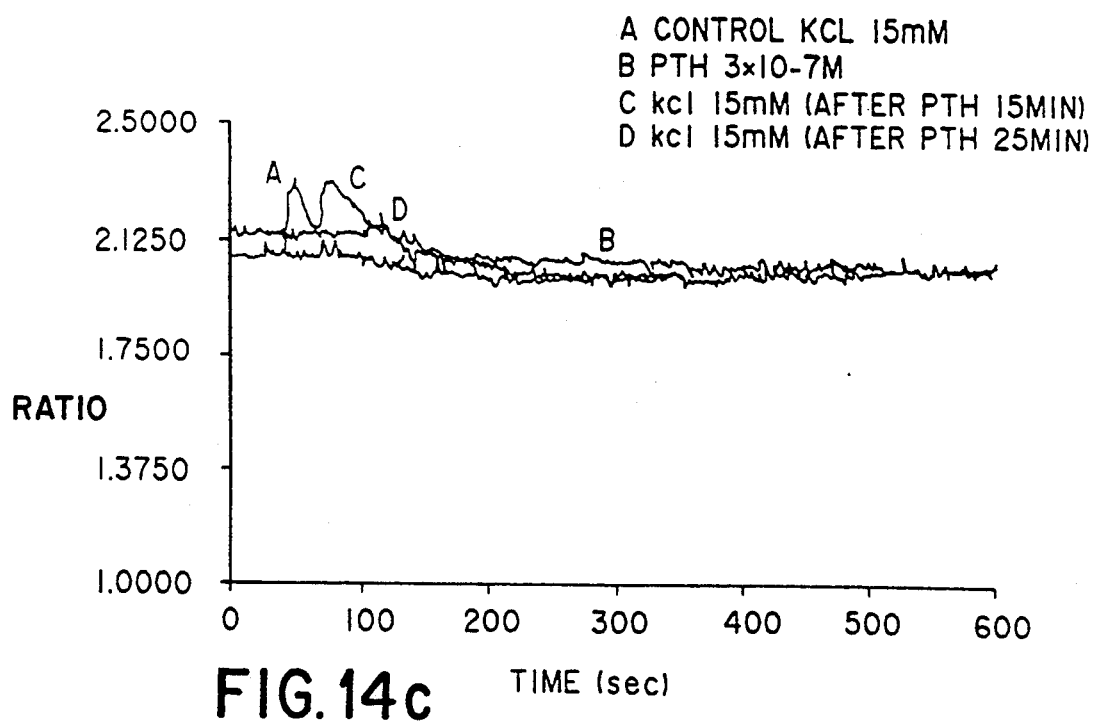
Figure 14:
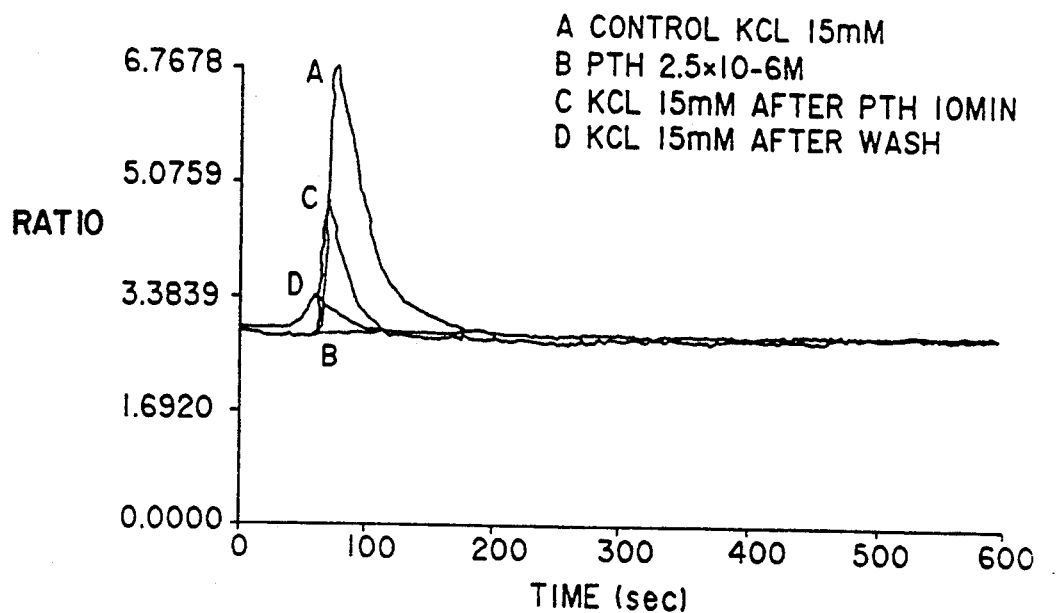
Figure 14:
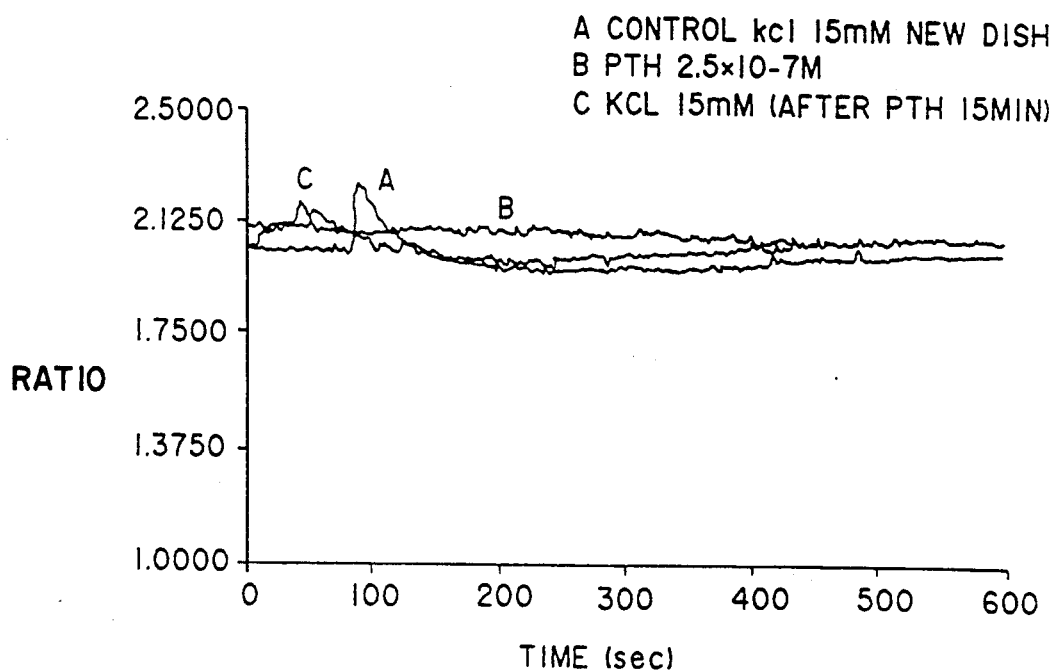
Figure 15:
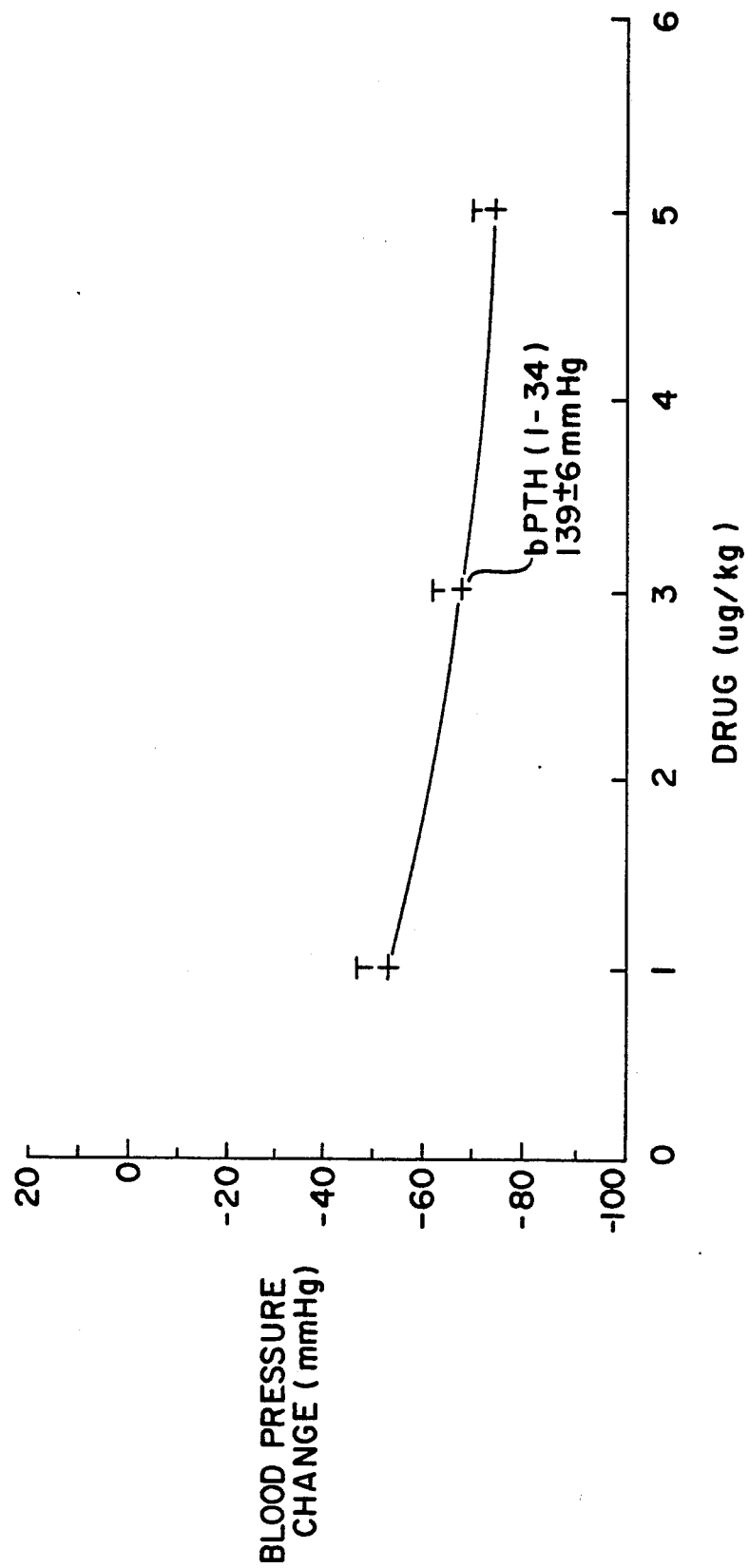
FIG. 15 shows the effect of Cs88 [bPTH- (1-34)] on the mean arterial blood pressure of anesthetized Sprague-Dawley rats. Blood pressure decreases as the dosage of the drug increases.

FIGS. 13, 14 a-d, 17, 18, 21, 22 and 23 illustrate the results of the above-described measurements when inhibitors such as an anti-osteoporotic agent (788) or bPTH-(1-34) or Cs114 were used in the presence of KCl.

As can be readily seen from the figures, the PTH analogues, whether full length or 1-34, which contain anomalous amino acids at positions twenty-five, twenty-six and twenty-seven (most particularly those which contain Ala$^{25}$—Ala$^{26}$—Ala$^{27}$), do not effect a hypotensive and smooth muscle relaxation response, including positive chronotropic effects, but do inhibit calcium uptake as stimulated by KCl in osteoblasts, which indicates that these compounds would have the same effect on bone cells as PTH and would be useful in the treatment of osteoporosis in mammals and, particularly, in man, without the aformentioned deleterious side effects in the elderly.

While not being bound by any theory, it is suggested that substitution Arg$^{25}$—Lys$^{26}$—Lys$^{27}$ by other amino acids in 1-84 PTH and in the 1-34 analogues removes the vasodepressor, smooth muscle relaxation and positive chronotropic and inotropic effects of either BPTH or HPTH. The effect on KCl induced calcium uptake in osteoblasts, however, is essentially unchanged for 1-84 or 1-34 PTH. In other words, the effect on bone cells is unchanged from PTH.

The physiological significance of an inhibiting effect on the KCl induced calcium uptake in bone cells is not yet understood. One hypothesis is that the analogues interact fully with bone cell receptor activity. The fact that the same effect is seen for both PTH and the analogues disclosed herein suggests that the site of interaction with the osteoblast cell receptor is unchanged by the substitution.

The analogues of the present invention can be used in the treatment of osteoporosis and other bone related diseases and disorders involving bone cell calcium regulation.

The analogues of the present invention may be administered to a warm-blooded mammalian in need thereof, particularly a human, by parental, topical, rectal administration or by inhalation. The analogues may be conventionally formulated in a parenteral dosage form compounding about 1 to about 300 mg per unit of dosage with a conventional vehicle, excipient, binder, preservative, stabilizer, color, agent or the like as called for by accepted pharmaceutical practice.

For parental administration, a 1 to 10 ml intravenous, intramuscular or subcutaneous injection would be given one to four times daily. The injection would contain an analogue of the present invention in an aqueous isotonic sterile solution or suspension optionally with a preservative such as phenol or a solubilizing agent such as ethylenediaminetetraacetic acid (EDTA). Among the acceptable vehicles and solvents that may be employed are water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as fixed oil in the preparation of injectables.

For rectal administration, the analogues of the present invention can be prepared in the form of suppositories by mixing with a suitable non-irritating excipient such as cocoa butter or polyethylene glycols.

For topical use, the analogues of the present invention can be prepared in the form of ointments, jellies, solutions, suspensions or dermal adhesive patches.

In a powdered aerosol, analogues of the present invention may be administered by a spinhaler turbo-inhaler device obtained from Fisons Corporation of Bedford, Mass., at a rate of about 0.1 to 50 mg per capsule, 1 to 8 capsules being administered daily for an average human. In a liquid aerosol, the compounds of the present invention are administered at the rate of about 100 to 1000 micrograms per "puff" or activated release of a standard volume of propellant. The liquid aerosol would be given at the rate of 1 to 8 "puffs" per day with variation in dosages due to the severity of the conditions being treated, the weight of the patient and the particle size distribution of the aerosol. A fluorinated hydrocarbon or isobutane find use as propellants for liquid aerosols.

Daily doses are in the range of about 0.01 to about 200 mg per kg of body weight, depending on the activity of the specific compound, the age, weight, sex and conditions of the subject to be treated, the type and severity of the disease, the frequency and route of administration. As would be well known, the amount of active ingredient that may be combined with the carried materials to produce a single dosage will vary depending upon the host treated and the particular mode of administration.

The following examples demonstrate the utility of applicants' invention. The examples are not limiting, but are illustrative only, and modifications which would be apparent to those skilled in the art are included within the scope of this disclosure.

EXAMPLE 1

In Vivo Blood Pressure Measurement.

Sprague-Dawley (S-D) rats were anaesthetized with pentobarbital and a cannula was inserted into the carotid artery. The rats were kept sedated during the procedure and were injected with PTH peptides only when the blood pressure of the rats were stable. Peptides were injected through a cannula in the jugular vein, in amounts of 1, 3 and 5 or more $\mu g/kg$ and the mean systolic and diastolic blood pressure was monitored continuously throughout the procedure. Results are reported with comparison to bPTH-(1-34).

EXAMPLE 2

In Vitro Rat Tail Artery Helical Strip Tension Assay

The assay was performed according to Pang et al., *Blood Vessels*, 22, 57 (1985). Sprague-Dawley rats were anaesthetized with pentobarbital and the tail artery excised and placed in ice-cold Krebs-Hanseleit solution (KHS) oxygenated with 95% $O_2$, 5% $CO_2$. Each artery was cut helically and strips of approximately 1.5 cm were secured in a Sawyer-Bartlestone chamber containing KHS. The force generated by the strips was measured with a Grass FT03 force displacement transducer and recorded on a polygraph. Isolated tail artery helical strips were equilibrated for 1 hour prior to use.

One to two minutes prior to addition of a peptide, the strips were contracted by addition of either arginine vasopressin (AVP), potassium chloride (KCl) or norepinephrine (NE) to the bath. The peptide was then added to the bath and the degree of relaxation measured. Bovine serum albumin was used as a control. Results are reported as percent decrease in tension for each drug and dose used. Drug dose is calculated on the basis of the final concentration in the bath solution.

EXAMPLE 3

In Vitro atrial contractility and contraction rate measurement

The assay was performed according to Tenner et al., *Canadian Journal of Physiology and Pharmacology*, Vol. 61, No. 10 (1983) pp. 1162-1167. Sprague-Dawley rats weighing between 100 and 250 g were treated with heparin (500 IU, i.p.) 15 minutes prior to decapitation. Thoracotomies were performed and the heart rapidly excised and placed in a cold physiological salt solution (PSS) having the following composition (in millimolar): NaCl, 120; KCl, 5.63; $CaCl_2$, 2.0; $MgCl_2$, 2.1; $NAHCO_3$, 25.0; dextrose, 9.7. The solution was continuously aerated by a gas mixture of 95% $O_2$-5% $CO_2$. The right atrium was isolated and suspended in a tissue chamber containing 20 mL of PSS at 37° C., pH 7.4. Atria were allowed to equilibrate for 1 hr under a resting tension of 1 g.

The atrial rate and force were determined from contractions recorded by a Grass FT.03 force-displacement transducer and a Grass model 79 polygraph. The Basial atrial rate f or control atria (as determined by counting the frequency of contractions) was $258 \pm 7$ bpm (n=29). Basal developed force of the spontaneously beating right atria was $0.33 \pm 0.06$ g (n=10). Dose-response curves for the peptides were obtained by cumulative addition of the respective peptides. Drug dose is calculated on the basis of the final concentration in the bath solution.

EXAMPLE 4

Measurement of Intracellular Free Calcium Concentration In vitro

Intracellular free calcium concentration was measured using the fluorescent dye FURA-2 according to the method of Grynkiewicz et al., *J. Biol. Chem.*, 260, 3440 (1985) and Pang et al., *P. N. A. S. (USA)*, 87, 623 (1990). UMR-106 rat osteosarcoma cells (ATCC CRL-1661) are incubated in 1-10 μM FURA-2 AM (Sigma Chemical Co., St. Louis), the acetomethoxy ester of FURA-2. Upon hydrolysis within the cell, FURA-2 is released which selectively binds to free $Ca^{2+}$. Binding to $Ca^{2+}$ shifts the fluorescent spectrum of FURA-2. Quantitation is obtained by exciting the dye at two different wavelengths, preferably 340 and 380 nm and measuring the fluorescent emission at 510 nm. The concentration of calcium is proportional to the ratio of the fluorescence emitted at 340 nm to that at 380 nm.

KCl is used in the medium to stimulate $[Ca^{2+}]_i$ increase.

After the intracellular $[Ca^{2+}]_i$ had been measured, the cells were washed with the original medium and the analogues added and the intracellular $[Ca^{2+}]_i$ measured again. KCl was then added without washing to measure the effect of the analogue on KCl induced $[Ca^{2+}]_i$ changes. After measurement, the cells were washed with the medium 3-4 times and KCl again added to determine the recovery of the cells after removal of the analogue. Results are shown by actual traces and histograms summarizing the results. As can be seen from FIGS. 14 *a–d*, PTH inhibits intracellar $[Ca^{2+}]_i$ increases as stimulated by KCl and measured by the method. FIGS. 18, 21, 22 and 23 illustrate comparable results for the $aa^{25,26,27}$ analogues.

The comparability of the analogues and PTH itself is considered to indicate that the analogues would be as useful as PTH for the treatment of osteoporosis.

TABLE I

| Designation | Length | Source | Substitution | Site |
|---|---|---|---|---|
| Cs88 | 1–34 | bovine | none | |
| Cs99 | 1–34 | bovine | Ala | 25 |
| Cs100 | 1–34 | bovine | Ala | 26 |
| Cs117 | 1–34 | bovine | Ala | 27 |
| Cs 221 | 1–34 | human | Ala | 25,26,27 |
| Cs1001 | 1–34 | human | none | |
| Cs2001 | 1–84 | human | none | |

---

We claim:

1. A bovine parathyroid hormone analogue having amino acid substitutions at three positions, consisting essentially of the structure shown in SEQ ID NO:3, wherein $Xaa^{25}$, $Xaa^{26}$ and $Xaa^{27}$ are each selected from the group consisting of Alanine (Ala), Isoleucine (Ile), Leucine (Leu), Methionine (Met), Phenylalanine (Phe), and Valine (Val).

2. The bovine parathyroid hormone analogue consisting essentially of the structure shown in SEQ ID NO:4.

3. A human parathyroid hormone analogue having amino acid substitutions at three positions, consisting essentially of the structure shown in SEQ ID NO: 5, wherein $Xaa^{25}$, $Xaa^{26}$ and $Xaa^{27}$ are each selected from the group consisting of Alanine (Ala), Isoleucine (Ile), Leucine (Leu), Methionine (Met), Phenylalanine (Phe), and Valine (Val).

4. The human parathyroid hormone analogue consisting essentially of the structure shown in SEQ ID NO:6.

5. A bovine parathyroid hormone analogue having amino acid substitutions at three positions, consisting essentially of the structure shown in SEQ ID NO:7, wherein $Xaa^{25}$, $Xaa^{26}$ and $Xaa^{27}$ are each selected from the group consisting of Alanine (Ala), Isoleucine (Ile), Leucine (Leu), Methionine (Met), Phenylalanine (Phe), and Valine (Val).

6. The bovine parathyroid hormone analogue consisting essentially of the structure shown in SEQ ID NO:8.

7. A human parathyroid hormone analogue having amino acid substitutions at three positions, consisting essentially of the structure shown in SEQ ID NO: 9, wherein $Xaa^{25}$, $Xaa^{26}$ and $Xaa^{27}$ are each selected from the group consisting of Alanine (Ala), Isoleucine (Ile), Leucine (Leu), Methionine (Met), Phenylalanine (Phe), and Valine (Val).

8. The human parathyroid hormone analogue consisting essentially of the structure shown in SEQ ID NO:10.

9. A pharmaceutical composition comprising a PTH analogue wherein amino acids at positions 25, 26 and 27 are substituted with an amino acid selected from the group consisting of Alanine (Ala), Isoleucine (Ile), Leucine (Leu), Methionine (Met), Phenylalanine (Phe), and Valine (Val), and a pharmaceutically acceptable carrier.

10. A method of treating osteoporosis in a patient in need of the treatment without causing substantial induction of hypotension, smooth muscle relaxation and cardiac inotropic and chronotropic action, said method comprising administering to said patient an osteoporotic treating effective amount of a PTH analogue wherein amino acids at positions 25, 26 and 27 are substituted with an amino acid selected from the group consisting of Alanine (Ala), Isoleucine (Ile), Leucine (Leu), Methionine (Met), Phenylalanine (Phe), and Valine (Val).

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ala Val Ser Glu Ile Gln Phe Met His Asn Leu Gly Lys His Leu Ser
 1               5                  10                  15

Ser Met Glu Arg Val Glu Trp Leu Arg Lys Lys Leu Gln Asp Val His
                20                  25                  30

Asn Phe Val Ala Leu Gly Ala Ser Ile Ala Tyr Arg Asp Gly Ser Ser
            35                  40                  45

Gln Arg Pro Arg Lys Lys Glu Asp Asn Val Leu Val Glu Ser His Gln
        50                  55                  60

Lys Ser Leu Gly Glu Ala Asp Lys Ala Asp Val Asp Val Leu Ile Lys
65                  70                  75                  80

Ala Lys Pro Gln
```

( 2 ) INFORMATION FOR SEQ ID NO:2:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
```

-continued

```
                    20                      25                      30

Asn  Phe  Val  Ala  Leu  Gly  Ala  Ser  Ile  Ala  Tyr  Arg  Asp  Gly  Ser  Ser
                       35                      40                      45

Gln  Arg  Pro  Arg  Lys  Lys  Glu  Asp  Asn  Val  Leu  Val  Glu  Ser  His  Gln
                  50                      55                      60

Lys  Ser  Leu  Gly  Glu  Ala  Asp  Lys  Ala  Asp  Val  Asp  Val  Leu  Ile  Lys
         65                      70                      75                           80

Ala  Lys  Pro  Gln
```

( 2 ) INFORMATION FOR SEQ ID NO:3:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
        Ala  Val  Ser  Glu  Ile  Gln  Phe  Met  His  Asn  Leu  Gly  Lys  His  Leu  Ser
         1                   5                      10                          15

Ser  Met  Glu  Arg  Val  Glu  Trp  Leu  Xaa  Xaa  Xaa  Leu  Gln  Asp  Val  His
                       20                      25                      30

Asn  Phe
```

( 2 ) INFORMATION FOR SEQ ID NO:4:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
        Ala  Val  Ser  Glu  Ile  Gln  Phe  Met  His  Asn  Leu  Gly  Lys  His  Leu  Ser
         1                   5                      10                          15

Ser  Met  Glu  Arg  Val  Glu  Trp  Leu  Ala  Ala  Ala  Leu  Gln  Asp  Val  His
                       20                      25                      30

Asn  Phe
```

( 2 ) INFORMATION FOR SEQ ID NO:5:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
        Ser  Val  Ser  Glu  Ile  Gln  Leu  Met  His  Asn  Leu  Gly  Lys  His  Leu  Asn
         1                   5                      10                          15

Ser  Met  Glu  Arg  Val  Glu  Trp  Leu  Xaa  Xaa  Xaa  Leu  Gln  Asp  Val  His
                       20                      25                      30

Asn  Phe
```

( 2 ) INFORMATION FOR SEQ ID NO:6:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide (x i) SEQUENCE DESCRIPTION: SEQ ID NO:6:

```
Ser Val Ser Glu Ile Gln Leu Met His Asn Leu Gly Lys His Leu Asn
1               5                   10                  15

Ser Met Glu Arg Val Glu Trp Leu Ala Ala Ala Leu Gln Asp Val His
            20              25                  30

Asn Phe
```

(2) INFORMATION FOR SEQ ID NO:7:

(i) SEQUENCE CHARACTERISTICS:
        (A) LENGTH: 84 amino acids
        (B) TYPE: amino acid
        (D) TOPOLOGY: linear (i i) MOLECULE TYPE: protein (x i) SEQUENCE DESCRIPTION: SEQ ID NO:7:

```
Ala Val Ser Glu Ile Gln Phe Met His Asn Leu Gly Lys His Leu Ser
1               5                   10                  15

Ser Met Glu Arg Val Glu Trp Leu Xaa Xaa Xaa Leu Gln Asp Val His
            20              25                  30

Asn Phe Val Ala Leu Gly Ala Ser Ile Ala Tyr Arg Asp Gly Ser Ser
        35              40                  45

Gln Arg Pro Arg Lys Lys Glu Asp Asn Val Leu Val Glu Ser His Gln
    50              55                  60

Lys Ser Leu Gly Glu Ala Asp Lys Ala Asp Val Asp Val Leu Ile Lys
65                  70              75                      80

Ala Lys Pro Gln
```

(2) INFORMATION FOR SEQ ID NO:8:

(i) SEQUENCE CHARACTERISTICS:
        (A) LENGTH: 84 amino acids
        (B) TYPE: amino acid
        (D) TOPOLOGY: linear (i i) MOLECULE TYPE: protein (x i) SEQUENCE DESCRIPTION: SEQ ID NO:8:

```
Ala Val Ser Glu Ile Gln Phe Met His Asn Leu Gly Lys His Leu Ser
1               5                   10                  15

Ser Met Glu Arg Val Glu Trp Leu Ala Ala Ala Leu Gln Asp Val His
            20              25                  30

Asn Phe Val Ala Leu Gly Ala Ser Ile Ala Tyr Arg Asp Gly Ser Ser
        35              40                  45

Gln Arg Pro Arg Lys Lys Glu Asp Asn Val Leu Val Glu Ser His Gln
    50              55                  60

Lys Ser Leu Gly Glu Ala Asp Lys Ala Asp Val Asp Val Leu Ile Lys
65                  70              75                      80

Ala Lys Pro Gln
```

(2) INFORMATION FOR SEQ ID NO:9:

(i) SEQUENCE CHARACTERISTICS:
        (A) LENGTH: 84 amino acids
        (B) TYPE: amino acid
        (D) TOPOLOGY: linear (i i) MOLECULE TYPE: protein (x i) SEQUENCE DESCRIPTION: SEQ ID NO:9:

```
Ser Val Ser Glu Ile Gln Leu Met His Asn Leu Gly Lys His Leu Asn
```

-continued

```
         1               5                    10                     15

Ser Met Glu Arg Val Glu Trp Leu Xaa Xaa Xaa Leu Gln Asp Val His
                      20              25              30

Asn Phe Val Ala Leu Gly Ala Ser Ile Ala Tyr Arg Asp Gly Ser Ser
              35                  40                  45

Gln Arg Pro Arg Lys Lys Glu Asp Asn Val Leu Val Glu Ser His Gln
          50              55                      60

Lys Ser Leu Gly Glu Ala Asp Lys Ala Asp Val Asp Val Leu Ile Lys
      65              70              75                      80

Ala Lys Pro Gln
```

( 2 ) INFORMATION FOR SEQ ID NO:10:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
      Ser Val Ser Glu Ile Gln Leu Met His Asn Leu Gly Lys His Leu Asn
      1               5                   10                      15

Ser Met Glu Arg Val Glu Trp Leu Ala Ala Ala Leu Gln Asp Val His
                      20              25              30

Asn Phe Val Ala Leu Gly Ala Ser Ile Ala Tyr Arg Asp Gly Ser Ser
              35                  40                  45

Gln Arg Pro Arg Lys Lys Glu Asp Asn Val Leu Val Glu Ser His Gln
          50              55                      60

Lys Ser Leu Gly Glu Ala Asp Lys Ala Asp Val Asp Val Leu Ile Lys
      65              70              75                      80

Ala Lys Pro Gln
```